bar code: US010924724B2

(12) United States Patent
Shioda et al.

(10) Patent No.: US 10,924,724 B2
(45) Date of Patent: Feb. 16, 2021

(54) MEDICAL STEREOSCOPIC OBSERVATION DEVICE, MEDICAL STEREOSCOPIC OBSERVATION METHOD, PROGRAM, AND MEDICAL STEREOSCOPIC OBSERVATION SYSTEM

(71) Applicants: Sony Olympus Medical Solutions Inc., Tokyo (JP); Sony Corporation, Tokyo (JP)

(72) Inventors: Keiji Shioda, Tokyo (JP); Manabu Koiso, Kanagawa (JP); Satoshi Mitsui, Aichi (JP)

(73) Assignees: SONY OLYMPUS MEDICAL SOLUTIONS INC., Tokyo (JP); SONY CORPORATION, Tokyo (JP)

(*) Notice: Subject to any disclaimer, the term of this patent is extended or adjusted under 35 U.S.C. 154(b) by 29 days.

(21) Appl. No.: 15/450,250

(22) Filed: Mar. 6, 2017

(65) Prior Publication Data
US 2017/0289528 A1 Oct. 5, 2017

(30) Foreign Application Priority Data

Mar. 29, 2016 (JP) ............... JP2016-065302

(51) Int. Cl.
H04N 13/296 (2018.01)
H04N 13/239 (2018.01)
H04N 13/302 (2018.01)
A61B 1/00 (2006.01)
A61B 1/04 (2006.01)

(52) U.S. Cl.
CPC ....... H04N 13/296 (2018.05); A61B 1/00193 (2013.01); A61B 1/04 (2013.01); H04N 13/239 (2018.05); H04N 13/302 (2018.05)

(58) Field of Classification Search
CPC .. H04N 13/296; H04N 13/302; H04N 13/239; A61B 1/00193; A61B 1/04
USPC .......................................................... 348/47
See application file for complete search history.

(56) References Cited

U.S. PATENT DOCUMENTS

2001/0017485 A1* 8/2001 Yoo .................. H02J 3/005
307/66
2003/0023888 A1* 1/2003 Smith .................. G06F 1/263
713/300

(Continued)

FOREIGN PATENT DOCUMENTS

JP 6-261341 A 9/1994
JP 2015-36060 A 2/2015
WO WO 2015/046081 A1 4/2015

OTHER PUBLICATIONS

Japanese Office Action dated Feb. 12, 2020, issued in corresponding Japanese Patent Application No. 2016-065302.

Primary Examiner — Joseph G Ustaris
Assistant Examiner — Matthew David Kim
(74) Attorney, Agent, or Firm — Xsensus LLP

(57) ABSTRACT

There is provided a medical stereoscopic observation device, including: an acquisition section that acquires a first signal associated with a first imaging section and a second signal associated with a second imaging section via mutually different transmission channels; and a switching section that switches a signal to use for a certain control between the first signal and the second signal, in accordance with a state of the transmission channel for transmitting the first signal.

19 Claims, 15 Drawing Sheets

(56) References Cited

U.S. PATENT DOCUMENTS

| | | | |
|---|---|---|---|
| 2006/0061560 A1* | 3/2006 | Yamashita | G09G 3/3233 345/204 |
| 2006/0126176 A1* | 6/2006 | Nogami | A61B 1/0005 359/464 |
| 2006/0161047 A1* | 7/2006 | Miyoshi | A61B 1/00091 600/157 |
| 2007/0156017 A1* | 7/2007 | Lamprecht | A61B 1/00193 600/102 |
| 2009/0268010 A1* | 10/2009 | Zhao | A61B 1/00009 348/45 |
| 2010/0111489 A1* | 5/2010 | Presler | H04N 5/225 386/278 |
| 2013/0229497 A1* | 9/2013 | Delacoux | H04N 13/296 348/47 |
| 2015/0359420 A1* | 12/2015 | Hatase | A61B 1/051 600/110 |
| 2016/0166345 A1* | 6/2016 | Kumar | A61B 34/37 606/130 |

* cited by examiner

MEDICAL STEREOSCOPIC OBSERVATION DEVICE, MEDICAL STEREOSCOPIC OBSERVATION METHOD, PROGRAM, AND MEDICAL STEREOSCOPIC OBSERVATION SYSTEM

CROSS REFERENCE TO RELATED APPLICATIONS

This application claims the benefit of Japanese Priority Patent Application JP 2016-065302 filed Mar. 29, 2016, the entire contents of which are incorporated herein by reference.

BACKGROUND

The present disclosure relates to a medical stereoscopic observation device, a medical stereoscopic observation method, a program, and a medical stereoscopic observation system.

Recently, due to advancements in surgical techniques and surgical equipment, surgeries for performing various treatments (also called microsurgery) while observing an affected site with an observation device for medical use, such as a surgical microscope or an endoscope, are coming to be conducted frequently. Also, such observation devices for medical use are not limited to devices that enable optical observation of the affected area, and also include devices that display an image of the affected area captured by an imaging section (camera) or the like as an electronic image on a display such as a monitor. For example, WO 2015/046081 discloses an example of a medical observation device capable of displaying an image of an affected area captured by an imaging section on a display as an electronic image.

In addition, when displaying, on a display, an image of an affected area captured by an imaging section of an observation device, the image often is displayed as a flat two-dimensional (2D) image. However, since a sense of perspective is difficult to obtain from a 2D image, and the relative distance between the affected area and a treatment tool may be difficult to grasp, in recent years, technology that displays a captured image of an affected area as a stereoscopic three-dimensional (3D) image has also been developed.

In this way, in an observation device that displays a captured image of an affected area as a stereoscopic 3D image (hereinafter designated a "stereoscopic observation device" in some cases), for example, images of an affected area from mutually different viewpoints (hereinafter also designated "viewpoint images") are captured by multiple imaging sections. Subsequently, by causing the viewpoint images captured by mutually different imaging sections to be observed by the left and right eyes, it becomes possible to enable a user to observe an image of the affected area as a stereoscopic 3D image based on the parallax between the viewpoint images.

SUMMARY

In a medical observation device, an event such as a failure in a transmission cable connecting an imaging section to an image processing device that performs various types of image processing on an image captured by the imaging section may cause a break in at least one of the transmission channels inside the transmission cable. Particularly, in the medical stereoscopic observation device discussed above, if a break occurs in the transmission channel connecting a subset of the imaging sections to the image processing device, acquiring a viewpoint image based on the captured results from an affected imaging section becomes difficult, thereby making it difficult to enable the user to observe a 3D image in some cases.

On the other hand, in a situation where higher reliability is demanded, like with medical equipment, there is demand for the display of the observation image (for example, a 3D image) to be maintained as much as possible, even under circumstances such as when one of the transmission channels fails.

Accordingly, the present disclosure proposes a medical stereoscopic observation device, a medical stereoscopic observation method, a program, and a medical stereoscopic observation system capable of continuing observation of an image captured by multiple imaging sections, even under circumstances such as when there is a break in one of the transmission channels connected to each of the multiple imaging sections.

According to an embodiment of the present disclosure, there is provided a medical stereoscopic observation device, including: an acquisition section that acquires a first signal associated with a first imaging section and a second signal associated with a second imaging section via mutually different transmission channels; and a switching section that switches a signal to use for a certain control between the first signal and the second signal, in accordance with a state of the transmission channel for transmitting the first signal.

Further, according to an embodiment of the present disclosure, there is provided a medical stereoscopic observation method, including: acquiring a first signal associated with a first imaging section and a second signal associated with a second imaging section via mutually different transmission channels; and switching, by a processor, a signal to use for a certain control between the first signal and the second signal, in accordance with a state of the transmission channel for transmitting the first signal.

Further, according to an embodiment of the present disclosure, there is provided a program causing a computer to execute: acquiring a first signal associated with a first imaging section and a second signal associated with a second imaging section via mutually different transmission channels; and switching a signal to use for a certain control between the first signal and the second signal, in accordance with a state of the transmission channel for transmitting the first signal.

Further, according to an embodiment of the present disclosure, there is provided a medical stereoscopic observation system, including: an imaging unit that includes a first imaging section and a second imaging section; an image processing device that performs image processing on images captured by the first imaging section and the second imaging section; a transmission cable that connects the imaging unit to the image processing device; an acquisition section that acquires a first signal associated with the first imaging section via a first transmission channel provided along the transmission cable, and acquires a second signal associated with the second imaging section via a second transmission channel different from the first transmission channel; and a switching section that switches a signal to use for a certain control between the first signal and the second signal, in accordance with a state of the first transmission channel.

According to an embodiment of the present disclosure as described above, there is provided a medical stereoscopic observation device, a medical stereoscopic observation method, a program, and a medical stereoscopic observation system capable of continuing observation of an image captured by multiple imaging sections, even under circumstances such as when there is a break in one of the transmission channels connected to each of the multiple imaging sections.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
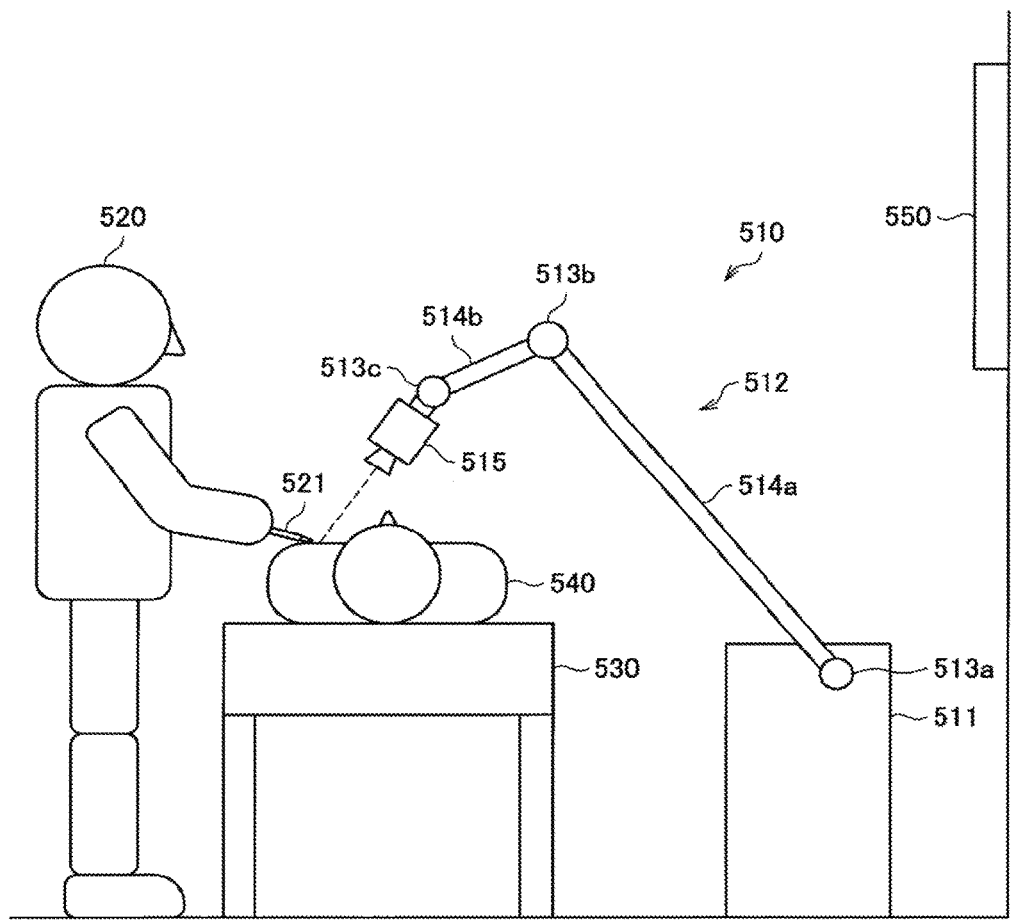
FIG. 1 is an explanatory diagram for explaining an example of a schematic configuration of a medical stereoscopic observation device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. Schematic configuration of medical stereoscopic observation device
2. Investigation of medical stereoscopic observation device
3. Functional configuration
4. Processes
5. Modifications
  5.1. Modification 1: modification of synchronization signal switching section
  5.2. Modification 2: control signal switching
  5.3. Modification 3: switching channel for acquiring information from each imaging section
6. Applied examples
  6.1. First applied example: rigid endoscopic device
  6.2. Second applied example: flexible endoscopic device
7. Hardware configuration
8. Conclusion

1. Schematic Configuration of Medical Stereoscopic Observation Device

First, to further elucidate the present disclosure, an example of a schematic configuration of a medical stereoscopic observation device according to an embodiment of the present disclosure will be described.

For example, FIG. 1 is an explanatory diagram for explaining an example of a schematic configuration of a medical stereoscopic observation device according to an embodiment of the present disclosure. FIG. 1 illustrates an example of a case for an applied example of using a medical stereoscopic observation device according to an embodiment of the present disclosure, in which a surgical video microscope device equipped with an arm is used as the medical stereoscopic observation device.

For example, FIG. 1 diagrammatically illustrates how a medical procedure is performed using a surgical video microscope device according to the present embodiment. Specifically, referring to FIG. 9, a state is illustrated in which a physician acting as the surgeon (user) 520 is using a surgical tool 521, such as a scalpel, tweezers, or forceps, for example, to perform surgery on a subject (patient) 540 lying on an operating table 530. Note that in the following description, medical procedure is used as a collective term to denote various types of medical treatments performed by a physician acting as the user 520 on a patient acting as the subject 540, such as a surgery or an examination. Also, although the example illustrated in FIG. 1 illustrates a situation of surgery as an example of a medical procedure, the medical procedure in which the surgical video microscope device 510 is used is not limited to surgery, and may be any of various other types of medical procedures such as an examination using an endoscope.

Beside the operating table 530, the surgical video microscope device 510 according to the present embodiment is provided. The surgical video microscope device 510 is equipped with a base section 511 which acts as a base, an arm section 512 which extends from the base section 511, and an imaging unit 515 connected as a front edge unit on the front edge of the arm section 512. The arm section 512 includes multiple joint sections 513a, 513b, and 513c, multiple links 514a and 514b joined by the joint sections 513a and 513b, and the imaging unit 515 provided on the front edge of the arm section 512. In the example illustrated in FIG. 1, for the sake of simplicity, the arm section 512 includes three joint sections 513a to 513c and two links 514a and 514b, but in actuality, the degrees of freedom in the positions and the orientations of the arm section 512 and the imaging unit 515 may be considered to appropriately configure factors such as the numbers and shapes of the joint sections 513a to 513c and the links 514a and 514b, and the directions of the drive shafts of the joints 513a to 513c, so as to achieve the desired degrees of freedom.

The joint sections 513a to 513c have a function of rotatably joining the links 514a and 514b to each other, and by driving the rotation of the joint sections 513a to 513c, the driving of the arm section 512 is controlled. Herein, in the following description, the position of each structural member of the surgical video microscope device 510 means the position (coordinates) in a space prescribed for drive control, while the orientation of each structural member means the direction (angle) with respect to an arbitrary axis in the space prescribed for drive control. Also, in the following description, the driving (or the drive control) of the arm section 512 refers to the driving (or the drive control) of the joint sections 513a to 513c, as well as to the position and orientation of each structural member of the arm section 512 being changed (or such change being controlled) by conducting the driving (or the drive control) of the joint sections 513a to 513c.

On the front edge of the arm section 512, the imaging unit 515 is connected as a front edge unit. The imaging unit 515 is a unit that acquires an image of an imaging target, and is a device such as a camera capable of capturing a moving image or a still image, for example. As illustrated in FIG. 1, the orientations and the positions of the arm section 512 and the imaging unit 515 are controlled by the surgical video microscope device 510 so that the imaging unit 515 provided on the front edge of the arm section 512 captures the operating site of the subject 540. Note that the configuration of the imaging unit 515 connected as the front edge unit on the front edge of the arm section 512 is not particularly limited, and the imaging unit 515 may be configured as an endoscope or a microscope, for example. Additionally, the imaging unit 515 may also be configured to be removable from the arm section 512. According to such a configuration, an imaging unit 515 depending on the usage scenario may be connected appropriately to the front edge of the arm section 512 as the front edge unit, for example. Note that although the description herein focuses on a case in which the imaging unit 515 is applied as the front edge unit, obviously the front edge unit connected to the front edge of the arm section 512 is not necessarily limited to the imaging unit 515.

Also, at a position facing the user 520, a display device 550 such as a monitor or a display is installed. An image of the operating site captured by the imaging unit 515 is displayed as an electronic image on the display screen of the display device 550. The user 520 performs various treatments while looking at an electronic image of the operating site displayed on the display screen of the display device 550.

In this way, in the medical field, the present embodiment proposes performing surgery while imaging the operating site with the surgical video microscope device 510.

Particularly, the surgical video microscope device 510 according to an embodiment of the present disclosure (that is, a medical stereoscopic observation device) is configured to be able to acquire image data for displaying the imaging target as a three-dimensional image (3D image).

As a specific example, the surgical video microscope device 510 is provided with a stereo camera including two imaging section subsystems (for example, camera units) as the imaging unit 515, and thereby acquires, via each imaging section, images from multiple different viewpoints (in other words, viewpoint images).

Each of the multiple viewpoint images acquired by the imaging unit 515 is subjected to various types of image processing by an image processing device built into or externally attached to the surgical video microscope device 510, and then displayed on the display device 550 as a left-eye image and a right-eye image, respectively. Note that in this description, the right-eye image denotes a so-called parallax image having a set parallax for observing a viewpoint corresponding to the user's right eye, to enable the user to observe a 3D image. Similarly, the left-eye image denotes a parallax image having a set parallax for observing a viewpoint corresponding to the user's left eye, to enable the user to observe a 3D image.

Note that a variety of techniques have been proposed as a mechanism for enabling the user 520 to observe, as a 3D image, the images displayed on the display device 550 as the left-eye image and the right-eye image. As a specific example, there is a technique in which special-purpose eyeglasses are used to cause the left and right eyes to observe mutually different images (in other words, a left-eye image and a right-eye image). Also, in recent years, glasses-free 3D picture technology which enables the observation of a three-dimensional image without the use of special-purpose eyeglasses has also been proposed.

In addition, the circumstances in which a medical observation device as described above is used also includes cases in which various information should be checked, including images of an affected area. Under such circumstances, usage patterns such as displaying images respectively on multiple displays or displaying multiple images inside a display may also be anticipated. As a specific example, a case is anticipated in which an overall picture of the affected area is displayed on one display, while an enlarged image of the affected area is displayed on another display. As another example, a case is also anticipated in which an image of the affected area is displayed on one display, while an image captured by another imaging device, such as a computed tomography (CT) image or a magnetic resonance imaging (MRI) image, is displayed on another display. For this reason, multiple display devices 550 may also be provided in some cases.

The above thus references FIG. 1 to describe, as an applied example of using a medical stereoscopic observation device according to an embodiment of the present disclosure, a an example of a case in which a surgical video microscope device equipped with an arm is used as the medical stereoscopic observation device.

2. Investigation of Medical Stereoscopic Observation Device

Next, to more easily understand the features of a medical stereoscopic observation device according the present embodiment, an example of a functional configuration of a typical medical stereoscopic observation device first will be described with reference to FIG. 2, followed by a summary of the challenges of a medical stereoscopic observation device according to the present embodiment. For example, FIG. 2 is a block diagram illustrating an example of a functional configuration of a medical stereoscopic observation device.

Figure 2:
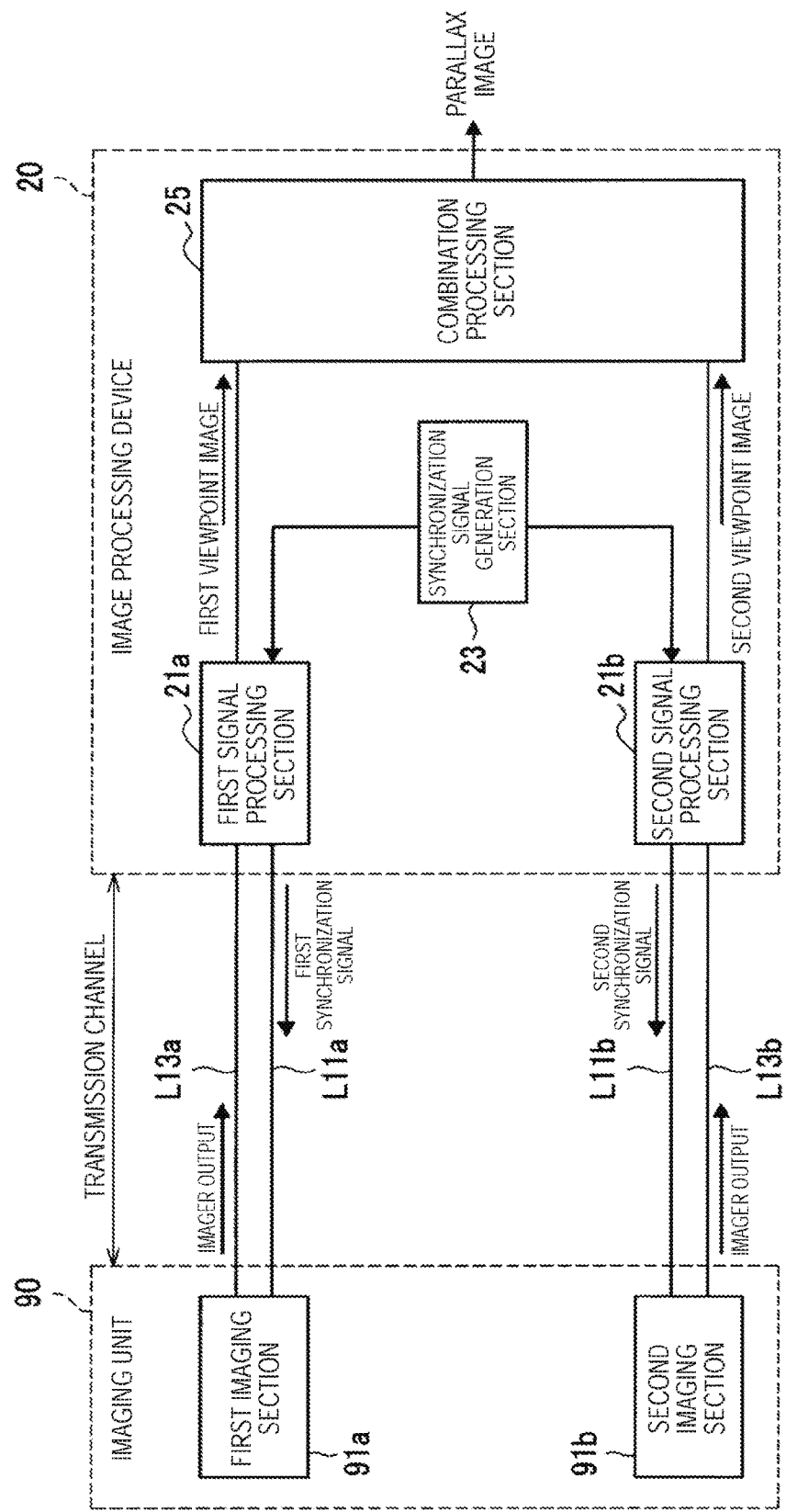
FIG. 2 is a block diagram illustrating an example of a functional configuration of a medical stereoscopic observation device.

As illustrated in FIG. 2, a medical stereoscopic observation device 9 includes an imaging unit 90 and an image processing device 20, for example. Also, although not illustrated in FIG. 2, the medical stereoscopic observation device 9 may also be provided with a display device (for example, the display device 550 illustrated in FIG. 1).

The imaging unit 90 corresponds to the imaging unit 515 of the surgical video microscope device 510 described with reference to FIG. 1, for example, and may be configured as a microscope, and may also be supported by a support section such as an arm, for example. Also, the image processing device 20 is configured to perform various types of image processing on images captured by the imaging unit 90. The image processing device 20 may be built into the base section 511 of the surgical video microscope device 510 described with reference to FIG. 1, or may be externally attached to the surgical video microscope device 510, for example. The imaging unit 90 and the image processing device 20 are connected via a transmission cable, for example, and by using various cable lines inside the transmission cable (such as metal wires or optical fibers, for example) as a transmission channel, exchange various information, such as control signals and imager output, with each other.

Note that at least part of the transmission cable connecting the imaging unit 90 and the image processing device 20 may be bendably configured, and may be supported by a support section such as an arm. According to such a configuration, even under circumstances in which the position or the orientation of the imaging unit 90 is continually adjusted by moving the arm, for example, it becomes possible to maintain the connected relationship (in other words, the exchange of information) between the imaging unit 90 and the image processing device 20.

At this point, the description will focus on a more detailed configuration of the imaging unit 90 and the image processing device 20. For example, the imaging unit 90 includes a first imaging section 91a and a second imaging section 91b. Each of the first imaging section 91a and the second imaging section 91b includes an image sensor, and an optical system for forming an image of an imaging target on the image sensor. The image sensor may be a device such as a complementary metal-oxide-semiconductor (CMOS) image sensor or a charge-coupled device (CCD) image sensor, for example. Also, the optical system includes various types of lenses, such as a focus lens and a zoom lens. Note that lenses included in the optical system may be configured to be movable on the optical axis. For example, by controlling the position on the optical axis of the focus lens, the position of the focal point of the optical system may be controlled. Also, by controlling the position on the optical axis of the zoom lens, the zoom magnification (in other words, the zoom position) of the optical system may be controlled.

Based on a configuration like the above, the first imaging section 91a and the second imaging section 91b capture an imaging target from mutually different viewpoints, and output the respectively captured viewpoint images to the image processing device 20 via the transmission cable. At this point, each of the first imaging section 91a and the second imaging section 91b operates in synchronization with the image processing device 20, based on a synchronization signal supplied from the image processing device 20 via the transmission cable. Specifically, each pixel constituting the image sensor generates a signal charge corresponding to the amount of light exposure, and temporarily holds the generated signal charge as a pixel signal. Note that the temporarily held pixel signals are read out in synchronization with a timing determined by a synchronization signal (such as a vertical synchronization signal or a horizontal synchronization signal, for example) supplied from the image processing device 20, and output as imager output to the image processing device 20 via the transmission cable.

For example, in the case of the example illustrated in FIG. 2, the first imaging section 91a operates in synchronization with a timing determined by a synchronization signal (hereinafter also designated the "first synchronization signal") supplied from the image processing device 20 via a transmission channel L11a provided inside the transmission cable. Subsequently, the first imaging section 91a outputs the imaging result of the subject by the image sensor (that is, the pixel signal generated by each pixel) as imager output to the image processing device 20 via a transmission channel L13a provided inside the transmission cable. Similarly, the second imaging section 91b operates in synchronization with a timing determined by a synchronization signal (hereinafter also designated the "second synchronization signal") supplied from the image processing device 20 via a transmission channel L11b provided inside the transmission cable. Subsequently, the second imaging section 91b outputs the imaging result of the subject by the image sensor as imager output to the image processing device 20 via a transmission channel L13b provided inside the transmission cable.

Next, the description will focus on the configuration of the image processing device 20. The image processing device 20 includes a first signal processing section 21a, a second signal processing section 21b, a synchronization signal generation section 23, and a combination processing section 25.

The first signal processing section 21a receives the supply of the first synchronization signal from the synchronization signal generation section 23 discussed later, and executes various processes in synchronization with the first synchronization signal. Specifically, the first signal processing section 21a outputs the first synchronization signal to the first imaging section 91a via the transmission channel L11a, and at a timing based on the first synchronization signal, receives imager output from the first imaging section 91a via the transmission channel L13a. Subsequently, the first signal processing section 21a generates an image of the viewpoint corresponding to the first imaging section 91a (in other words, a viewpoint image) based on the imager output from the first imaging section 91a, and outputs the generated viewpoint image (hereinafter also designated the "first viewpoint image") to the combination processing section 25.

Similarly, the second signal processing section 21b receives the supply of the second synchronization signal from the synchronization signal generation section 23, and executes various processes in synchronization with the second synchronization signal. Specifically, the second signal processing section 21b outputs the second synchronization signal to the second imaging section 91b via the transmission channel L11b, and at a timing based on the second synchronization signal, receives imager output from the second imaging section 91b via the transmission channel L13b. Subsequently, the second signal processing section 21b generates an image of the viewpoint corresponding to the second imaging section 91b based on the imager output from the second imaging section 91b, and outputs the generated viewpoint image (hereinafter also designated the "second viewpoint image") to the combination processing section 25.

Note that each of the first signal processing section 21a and the second signal processing section 21b may also perform various types of image processing on a generated viewpoint image, and outputs the processed viewpoint image to the combination processing section 25. Note that the image processing performed on each viewpoint image may be processing such as processing that enhances a certain target, and processing related to correcting brightness or contrast, for example.

The synchronization signal generation section 23 includes components such as a signal generator circuit that oscillates at a desired frequency, for example, and generates synchronization signals (namely, the first synchronization signal and the second synchronization signal discussed earlier), and supplies the generated synchronization signals to the first signal processing section 21a and the second signal processing section 21b. By supplying synchronization signals from the synchronization signal generation section 23 to both the first signal processing section 21a and the second signal processing section 21b in this way, it becomes possible to synchronize the respective processes between the first signal processing section 21a and the second signal processing section 21b (and by extension, between the first imaging section 91a and the second imaging section 91b).

The combination processing section 25 acquires, from the first signal processing section 21a and the second signal processing section 21b, viewpoint images generated on the basis of the imaging results by the first imaging section 91a and the second imaging section 91b, respectively. Subsequently, based on the acquired viewpoint images, the combination processing section 25 generates a parallax image having a set parallax enabling the user to observe a 3D image.

At this point, as an example of a more detailed process by the combination processing section 25, a process in the case of enabling the user to observe a 3D on the basis of glasses-free 3D picture technology will be described. In this case, for example, the combination processing section 25 computes a parallax value to set in the image depicting each viewpoint, based on an anticipated space between the user's viewpoints (in other words, the space between the left eye and the right eye). Subsequently, the combination processing section 25 generates a desired multiview image presented on the basis of the computed results of the parallax value by the viewpoint images observed by the user's left and right eyes, respectively, and causes the generated multiview image to be displayed on a certain display device (for example, the display device 550 illustrated in FIG. 1). The respective viewpoint images presented in the multiview image (that is, the left-eye image and the right-eye image) are separated by an optical member such as a lenticular sheet or a parallax barrier provided on the display device, for example, and the respective viewpoint images are observed at the user's corresponding viewpoints (that is, the left eye and the right eye). Consequently, the user becomes able to observe a 3D image via the display device.

Note that the process for enabling observation of a 3D image described above is merely one example, and obviously may be modified as appropriate in accordance with the technique or configuration for enabling observation of a 3D image.

The above thus describes an example of a functional configuration of a typical medical stereoscopic observation device with reference to FIG. 2.

Note that for the transmission cable connecting the imaging unit 10 and the image processing device 20, a comparatively long cable of 1 m or more may be used in some cases. Also, due to the movement of the arm and the like, the transmission cable may be curved or bent in many circumstances. For this reason, a failure or the like in the transmission cable may cause a break in at least one of the transmission channels from among the transmission channels between the imaging unit 10 and the image processing device 20 in some cases. For example, if there is a break in the transmission channel L11a from among the transmission channels illustrated in FIG. 2, it may become difficult to supply the first synchronization signal to the first imaging section 91a. Under such circumstances, it may be difficult for the first imaging section 91a to maintain operations related to capturing images in some cases. For this reason, generating the first viewpoint image may become difficult, and by extension, generating a parallax image enabling observation of a 3D image may become difficult.

On the other hand, in a situation where higher reliability is demanded, like a situation in which a medical stereoscopic observation device according to the present embodiment is used, there is demand for the display of the image (for example, a 3D image) to be maintained as much as possible, even under circumstances such as when one of the transmission channels fails as above. Accordingly, the present disclosure proposes one example of a mechanism in a medical stereoscopic observation device enabling the continuation of observation of an image captured by multiple imaging sections, even under circumstances such as when there is a break in one of the transmission channels connected to each of the multiple imaging sections.

3. Functional Configuration

First, an example of a functional configuration of a medical stereoscopic observation device according to an embodiment of the present disclosure will be described with reference to FIGS. 3 and 4. For example, FIG. 3 is a block diagram illustrating an example of a functional configuration of a medical stereoscopic observation device according to the present embodiment.

Figure 3:
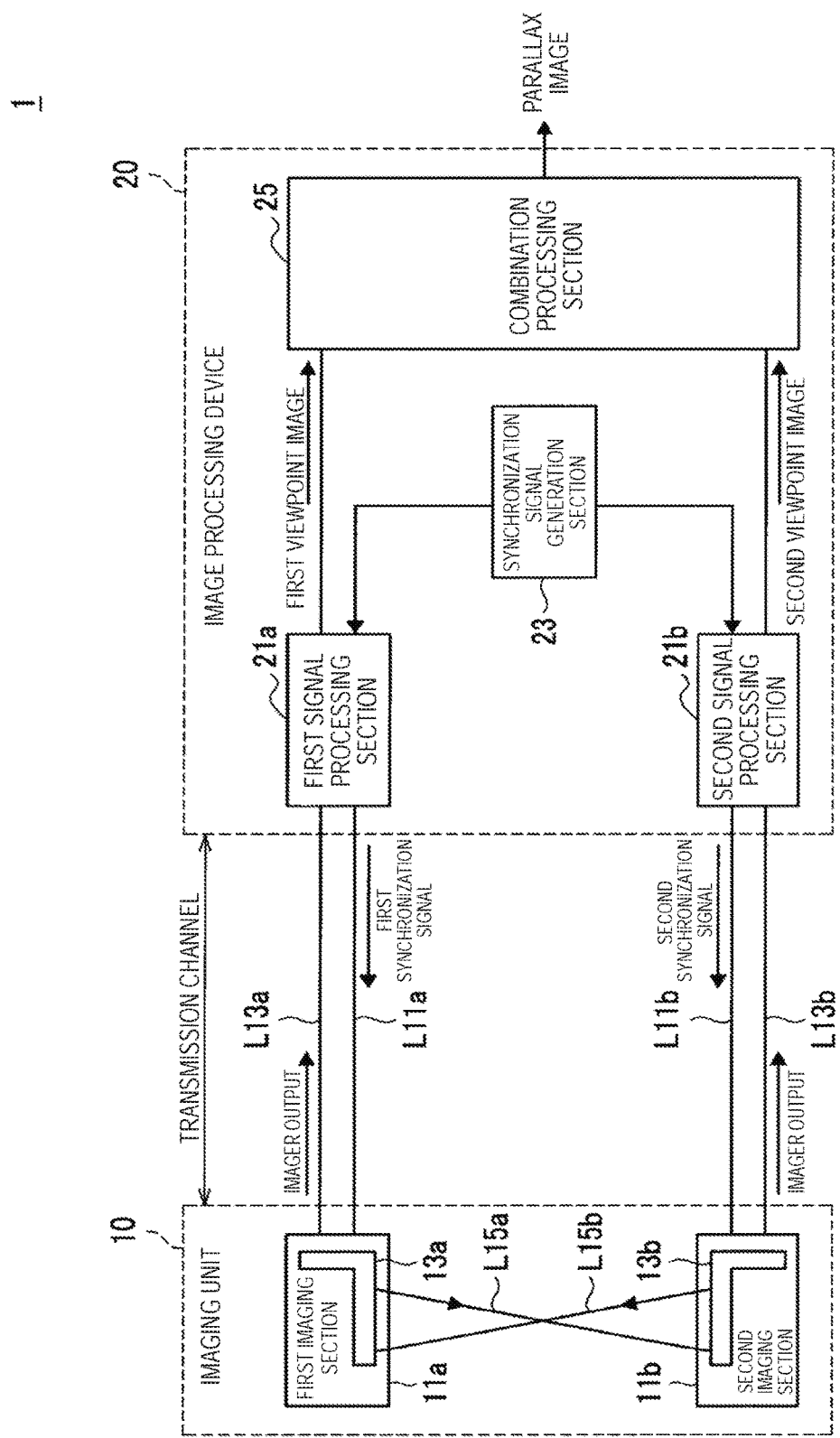
FIG. 3 is a block diagram illustrating an example of a functional configuration of a medical stereoscopic observation device according to an embodiment.

As illustrated in FIG. 3, the medical stereoscopic observation device 1 according to the present embodiment includes an imaging unit 10 and an image processing device 20. Also, although not illustrated in FIG. 3, the medical stereoscopic observation device 1 may also be provided with a display device (for example, the display device 550 illustrated in FIG. 1). Note that as illustrated in FIG. 3, in the medical stereoscopic observation device 1 according to the present embodiment, the configuration of the imaging unit 10 differs from the medical stereoscopic observation device 9 discussed earlier with reference to FIG. 2, whereas the rest of the configuration (for example, the image processing device 20) is similar to the medical stereoscopic observation device 9. For this reason, the following description will focus primarily on the configuration of the imaging unit 10, and detailed description will be reduced or omitted for parts of the configuration that are substantially similar to the medical stereoscopic observation device 9 illustrated in FIG. 2.

As illustrated in FIG. 3, the imaging unit 10 includes a first imaging section 11a and a second imaging section 11b. Note that the first imaging section 11a and the second imaging section 11b have configurations corresponding to the first imaging section 91a and the second imaging section 91b of the imaging unit 90 in the medical stereoscopic observation device 9 illustrated in FIG. 2.

In addition, in the imaging unit 10 according to the present embodiment, each of the first imaging section 11a and the second imaging section 11b includes a synchronization signal switching section 13. Note that in the following description, when distinguishing between the synchronization signal switching sections 13 of the first imaging section 11a and the second imaging section 11b, respectively, the first imaging section 11a side will be designated the "synchronization signal switching section 13a", while the second imaging section 11b side will be designated the "synchronization signal switching section 13b". The synchronization signal switching sections 13a and 13b are interconnected via transmission channels L15a and L15b. Note that the transmission channels L15a and L15b may simply interconnect the synchronization signal switching sections 13a and 13b inside the imaging unit 10, and are formed to be comparatively shorter than the transmission channels L11a and L11b provided in the transmission cable. The transmission channels L15a and L15b may be traces formed on a printed circuit board or the like, for example.

The synchronization signal switching section 13a is supplied with the first synchronization signal associated with the first imaging section 11a from the image processing device 20 via the transmission channel L11a provided inside the transmission cable. Also, the first synchronization signal supplied via the transmission channel L11a is split, and one part of the split first synchronization signal is also supplied to the synchronization signal switching section 13b via the transmission channel L15a. Similarly, the synchronization signal switching section 13b is supplied with the second synchronization signal associated with the second imaging section 11b from the image processing device 20 via the transmission channel L11b provided inside the transmission cable. Also, the second synchronization signal supplied via the transmission channel L11b is split, and one part of the split second synchronization signal is also supplied to the synchronization signal switching section 13a via the transmission channel L15b. According to a configuration like the above, it becomes possible to supply each of the synchronization signal switching sections 13a and 13b with both the first synchronization signal and the second synchronization signal via mutually different transmission channels.

Subsequently, the synchronization signal switching section 13a switches the synchronization signal to supply to the first imaging section 11a between the first synchronization signal and the second synchronization signal, in accordance with the state of the transmission channel L11a provided inside the transmission cable (in other words, the supply state of the first synchronization signal). Similarly, the synchronization signal switching section 13b switches the synchronization signal to supply to the second imaging section 11b between the first synchronization signal and the second synchronization signal, in accordance with the state of the transmission channel L11b provided inside the transmission cable (in other words, the supply state of the second synchronization signal).

At this point, a more detailed configuration of the synchronization signal switching section 13 will be described with reference to FIG. 4. FIG. 4 is a block diagram illustrating an example of a functional configuration of the synchronization signal switching section 13 according to the present embodiment. Note that the synchronization signal switching sections 13a and 13b have a substantially similar configuration, except for differences in the supply source of the first synchronization signal and the second synchronization signal, and the supply destination of the synchronization signal. For this reason, the following description will focus on the synchronization signal switching section 13a side, while a detailed description of the synchronization signal switching section 13b will be reduced or omitted.

Figure 4:
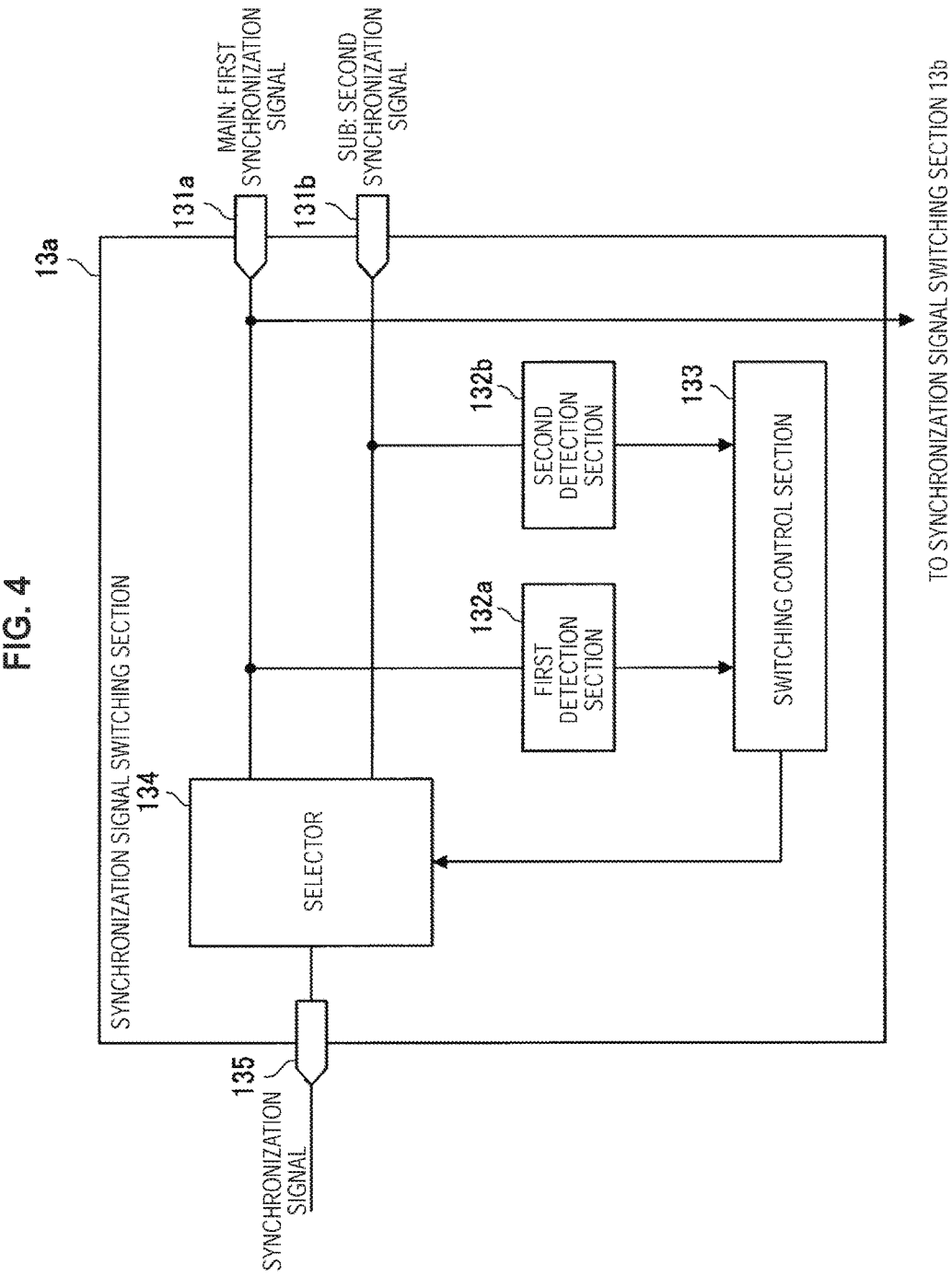
FIG. 4 is a block diagram illustrating an example of a functional configuration of a synchronization signal switching section according to an embodiment.

As illustrated in FIG. 4, the synchronization signal switching section 13a includes input terminals 131a and 131b, a first detection section 132a and a second detection section 132b, a switching control section 133, a selector 134, and an output terminal 135. The input terminal 131a is an input terminal that accepts the input of a synchronization signal supplied via a transmission channel provided inside the transmission cable as a main synchronization signal. Also, the input terminal 131b is an input terminal that accepts the input of the synchronization signal supplied from the other synchronization signal switching section 13 side as a sub synchronization signal. In other words, in the synchronization signal switching section 13a, the first synchronization signal supplied via the transmission channel L11a illustrated in FIG. 3 is input into the input terminal 131a. Meanwhile, the second synchronization signal supplied via the transmission channel L15b is input into the input terminal 131b.

The first synchronization signal input into the input terminal 131a is split by a splitter or the like, with one part being input into the selector 134, and another part being input into the first detection section 132a. Also, a part of the split first synchronization signal is supplied to the synchronization signal switching section 13b side via the transmission channel L15a illustrated in FIG. 3. Meanwhile, the second synchronization signal input into the input terminal 131b is split by a splitter or the like, with one part being input into the selector 134, and another part being input into the second detection section 132b.

Each of the first detection section 132a and the second detection section 132b detects an input synchronization signal to thereby detect the presence or absence of the input of the synchronization signal, and notifies the switching control section 133 of the detection result. As a specific example, if there is a break in the transmission channel L11a illustrated in FIG. 3 because of damage to the transmission cable or the like, a state occurs in which the first synchronization signal is not input into the input terminal 131a. In other words, the first detection section 132a detects that the first synchronization signal is not being input, and notifies the switching control section 133 of the detection result (that is, the first synchronization signal is not being input).

The selector 134 selectively switches the synchronization signal to be output from the output terminal 135 between the main synchronization signal input via the input terminal 131a (that is, the first synchronization signal) and the sub synchronization signal input via the input terminal 131b (that is, the second synchronization signal). Note that the synchronization signal output from the output terminal 135 is supplied to the first imaging section 11a. The switching-related operation of the selector 134 is controlled by the switching control section 133.

The switching control section 133 controls the switching-related operation of the selector 134, in accordance with a detection result of the presence or absence of a synchronization signal by each of the first detection section 132a and the second detection section 132b. As a specific example, if the first detection section 132a detects the input of the main synchronization signal (that is, the first synchronization signal), the switching control section 133 controls the switching-related operation of the selector 134 so that the main synchronization signal is output from the output terminal 135. Meanwhile, as another example, if the first detection section 132*a* does not detect the input of the main synchronization signal, the switching control section 133 controls the switching-related operation of the selector 134 so that the sub synchronization signal (that is, the second synchronization signal) is output from the output terminal 135.

Meanwhile, circumstances may be anticipated in which the interruption of the main synchronization signal is temporary, and after the switching-related operation of the selector 134 is controlled so that the sub synchronization signal is output from the output terminal 135, the input of the main synchronization signal is detected again. In such a case, the switching control section 133 may also control the switching-related operation of the selector 134 again so that the main synchronization signal is output from the output terminal 135.

Based on a configuration like the above, the synchronization signal switching section 13*a* recognizes the supply state of each of the main synchronization signal and the sub synchronization signal, and in accordance with the recognition result, switches the synchronization signal to be supplied to the first imaging section 11*a* between the main synchronization signal and the sub synchronization signal. According to such a configuration, even under circumstances in which the supply of the main synchronization signal breaks, for example, the synchronization signal switching section 13*a* is still able to supply the sub synchronization signal to the first imaging section 11*a* instead of the main synchronization signal. For this reason, even if there is a break in the transmission channel L11*a* illustrated in FIG. 3 because of damage to the transmission cable or the like, and supplying the first synchronization signal to the first imaging section 11*a* becomes difficult, for example, supplying the second synchronization signal makes it possible to continue capturing images with the first imaging section 11*a*. In addition, this configuration is not limited to a break in communication, and the synchronization signal switching section 13*a* may also switch the synchronization signal to be supplied to the first imaging section 11*a* between the main synchronization signal and the sub synchronization signal in accordance with a degradation in communication quality. In this case, it is sufficient for the synchronization signal switching section 13*a* to monitor the communication quality of the main synchronization signal (for example, the noise level expressed by the S/N ratio or the like), for example, and in the case of recognizing a degradation of communication quality based on the monitoring result, switch the synchronization signal to be supplied to the first imaging section 11*a* between the main synchronization signal and the sub synchronization signal.

FIG. 3 will now be referenced again. The first imaging section 11*a* operates in synchronization with a timing determined by the synchronization signal supplied from the synchronization signal switching section 13*a*. In addition, the first imaging section 11*a* outputs the imaging result of the subject by the image sensor as imager output to the image processing device 20 via the transmission channel L13*a*. Similarly, the second imaging section 11*b* operates in synchronization with a timing determined by the synchronization signal supplied from the synchronization signal switching section 13*b*. In addition, the second imaging section 11*b* outputs the imaging result of the subject by the image sensor as imager output to the image processing device 20 via the transmission channel L13*b*.

The foregoing thus references FIGS. 3 and 4 to describe an example of a functional configuration of a medical stereoscopic observation device according to an embodiment of the present disclosure, with particular focus on the configuration that differs from the medical stereoscopic observation device 9 illustrated in FIG. 2.

Note that the configuration of a medical stereoscopic observation device described with reference to FIG. 3 is merely one example, and the configuration is not necessarily limited solely to the example illustrated in FIG. 3. For example, the number of imaging sections included in the imaging unit 10 is not limited only to the case of two as illustrated in FIG. 3, and three or more imaging sections may also be provided, for example. In this case, it is sufficient to provide each imaging section with respective transmission channels so that a synchronization signal associated with the imaging section (in other words, a main synchronization signal) and synchronization signals associated with the other imaging sections (in other words, sub synchronization signals) are supplied, and the synchronization signal switching section 13 discussed earlier. Additionally, it is sufficient for the synchronization signal switching section 13 to switch the synchronization signal to be supplied to the imaging section between the main synchronization signal and the sub synchronization signals, in accordance with the supply state of each synchronization signal (in other words, the state of the transmission channel by which each synchronization signal is supplied). Also, as discussed earlier, the imaging section supplied with a synchronization signal, reads out pixel signals held in each pixel constituting the image sensor, based on a timing determined by the synchronization signal. Furthermore, the imaging section may also control the timing at which to transmit the read-out pixel signals as imager output to the image processing device 20 via the transmission cable, based on a timing determined by the supplied synchronization signal.

Additionally, if the respective components of the image processing device 20 are able to realize the functions discussed above, the configuration of at least part of these respective components may also be provided in a different device from the other components. As a specific example, the first signal processing section 21*a*, the second signal processing section 21*b*, the synchronization signal generation section 23, and the combination processing section 25 may also be provided in different devices from each other.

4. Processes

Figure 5:
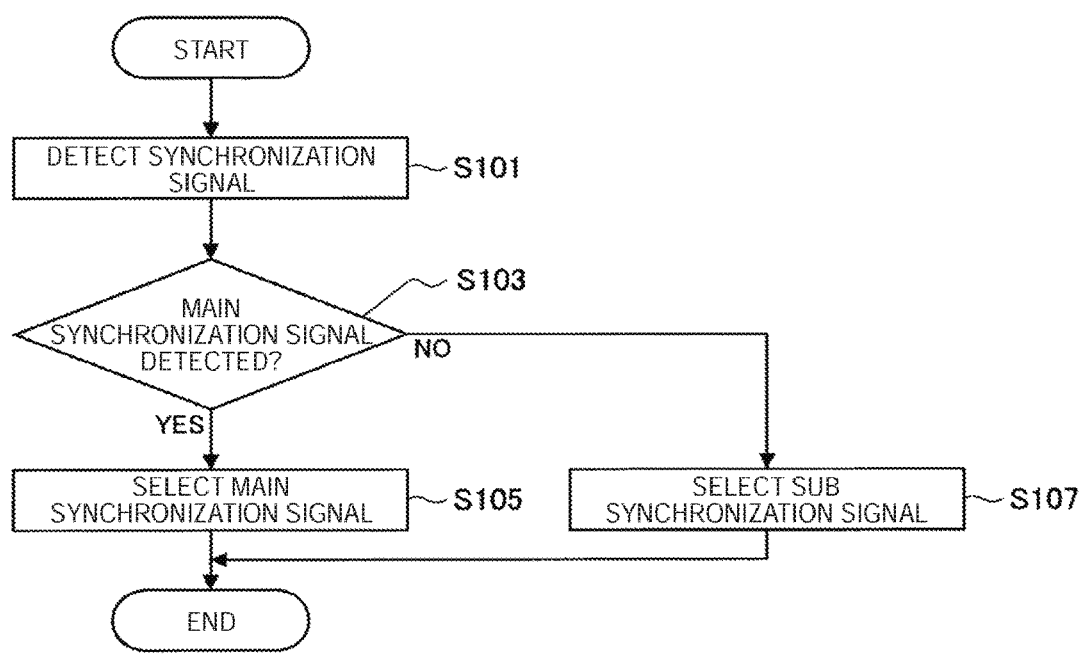
FIG. 5 is a flowchart illustrating an example of the operation of a synchronization signal switching section in a medical stereoscopic observation device according to an embodiment.

Next, an example of a process conducted by a medical stereoscopic observation device according to the present embodiment will be described with reference to FIG. 5, with particular focus on a process conducted by the synchronization signal switching section 13. FIG. 5 is a flowchart illustrating an example of the operation of a synchronization signal switching section in a medical stereoscopic observation device according to the present embodiment. Note that for the synchronization signal switching section 13*a* on the first imaging section 11*a* side and the synchronization signal switching section 13*b* on the second imaging section 11*b* side, the flow of the process is substantially similar, except for the different correspondence relationship between the main and sub synchronization signals, and the first and second synchronization signals. For this reason, the following description will focus on the operation of the synchronization signal switching section 13*a* on the first imaging section 11*a* side, while a detailed description of the synchronization signal switching section 13*b* on the second imaging section 11*b* side will be reduced or omitted.

The synchronization signal switching section 13a receives the supply of the main synchronization signal (first synchronization signal) via the transmission channel L11a provided inside the transmission cable. Also, the synchronization signal switching section 13a receives the supply of the sub synchronization signal (second synchronization signal) via the transmission channel L15b from the synchronization signal switching section 13b side. Based on such a configuration, the synchronization signal switching section 13a detects the presence or absence of the input of each of the main synchronization signal and the sub synchronization signal (S101).

Subsequently, for example, if the input of the main synchronization signal is detected (S103, Yes), the synchronization signal switching section 13a selects the main synchronization signal (S105). On the other hand, if the input of the main synchronization signal is not detected (S103, No), the synchronization signal switching section 13a selects the sub synchronization signal (S107). Subsequently, the synchronization signal switching section 13a supplies the selected synchronization signal to the first imaging section 11a.

The above thus describes an example of a process conducted by a medical stereoscopic observation device according to the present embodiment with reference to FIG. 5, with particular focus on a process conducted by the synchronization signal switching section 13.

5. Modifications

Next, modifications of a medical stereoscopic observation device according to the present embodiment will be described.

<5.1. Modification 1: Modification of Synchronization Signal Switching Section>

First, modifications of the synchronization signal switching section 13 discussed earlier with reference to FIG. 4 will be described as Modification 1. Note that in each modification of the synchronization signal switching section 13 described hereinafter, the synchronization signal switching sections respectively included in the first imaging section 11a and the second imaging section 11b have a substantially similar configuration, except for the different correspondence relationship between the main and sub synchronization signals, and the first and second synchronization signals. For this reason, the following description will focus on the synchronization signal switching section on the first imaging section 11a side, while a detailed description of the synchronization signal switching section on the second imaging section 11b side will be reduced or omitted.

(Modification 1-1)

Figure 6:
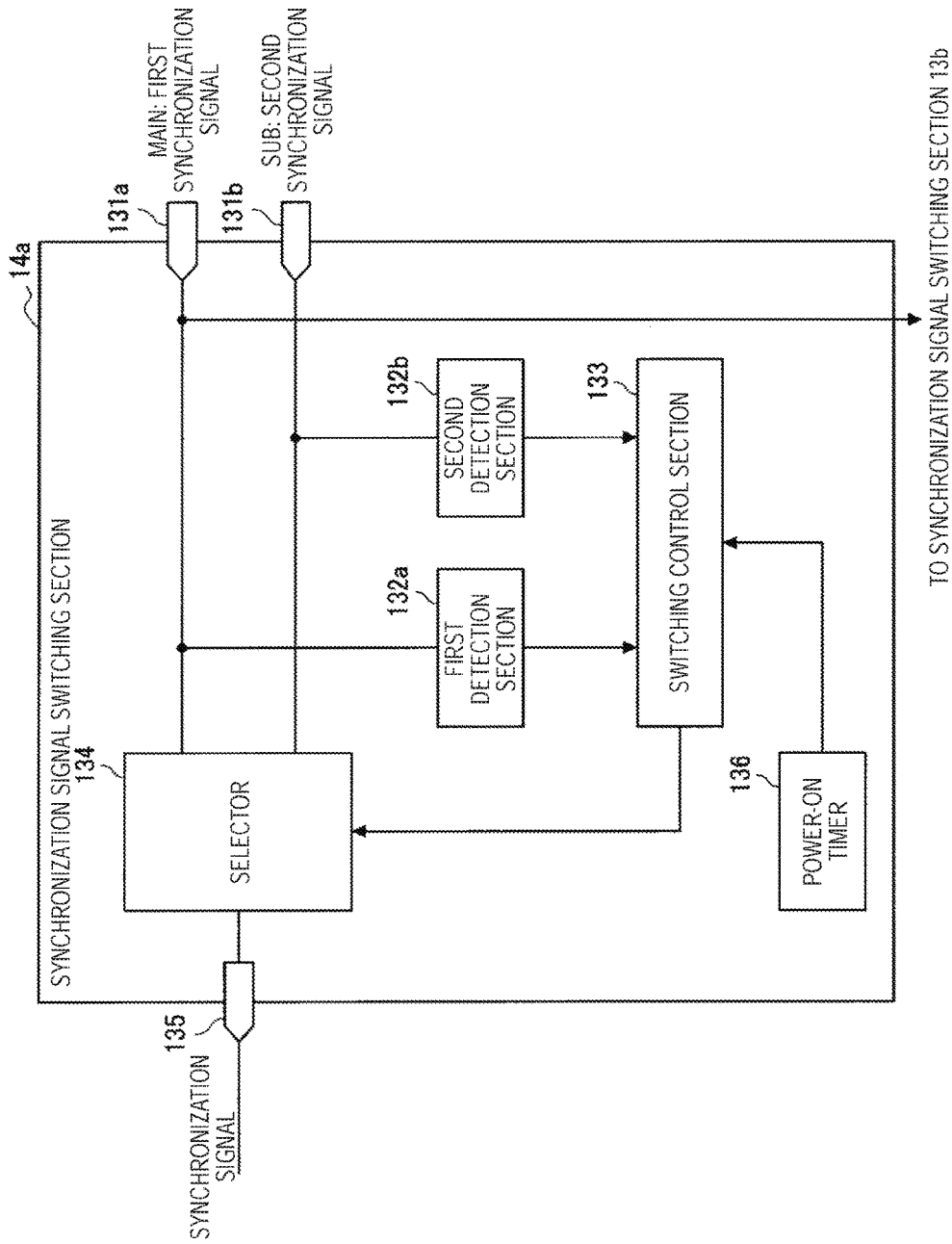
FIG. 6 is an explanatory diagram for explaining an example of a medical stereoscopic observation device according to Modification 1-1.

For example, FIG. 6 is an explanatory diagram for explaining an example of a medical stereoscopic observation device according to Modification 1-1, and is a block diagram illustrating a functional configuration of a modification of the synchronization signal switching section. Note that the synchronization signal switching section illustrated in FIG. 6 may be designated the "synchronization signal switching section 14a" in some cases, to distinguish from the synchronization signal switching section 13a according to the foregoing embodiment.

When the main synchronization signal is supplied normally, for example, the synchronization signal switching section 13a discussed earlier with reference to FIG. 4 supplies the main synchronization signal (first synchronization signal) to the first imaging section 11a. Additionally, if there is a break in the supply of the main synchronization signal, instead of the main synchronization signal, the synchronization signal switching section 13a supplies the first imaging section 11a with the sub synchronization signal (second synchronization signal), which is different from the main synchronization signal and which is transmitted via a different transmission channel. According to such a configuration, even under circumstances in which there is a break in the supply of the main synchronization signal due to a break or the like in one of the transmission channels, it is possible to continue capturing images with the first imaging section 11a.

On the other hand, immediately after the medical stereoscopic observation device is powered on, the supply of the synchronization signal from the image processing device 20 to the imaging unit 10 may not necessarily be stable. For this reason, for example, circumstances are anticipated in which first only the sub synchronization signal (second synchronization signal) arrives at the synchronization signal switching section 13a, and later, the main synchronization signal (first synchronization signal) arrives. Under such circumstances, a situation is also anticipated in which the synchronization signal to be supplied to the first imaging section 11a first is switched to the sub synchronization signal, and later, is switched again to the main synchronization signal. In some cases, capturing an image of the subject at the timing when such switching occurs may be difficult. In light of such circumstances, in the synchronization signal switching section 14a illustrated in FIG. 6, the operation related to switching the synchronization signal is restrained until the supply of the synchronization signal stabilizes immediately after power-on, thereby stabilizing the operation related to capturing an image of the subject.

Specifically, as illustrated in FIG. 6, the synchronization signal switching section 14a differs from the synchronization signal switching section 13a discussed earlier with reference to FIG. 4 by being provided with a power-on timer 136. Accordingly, the following description will focus on the portion of the configuration of the synchronization signal switching section 14a that is different from the synchronization signal switching section 13a discussed earlier, while a detailed description of the portion that is substantially similar to the synchronization signal switching section 13a will be reduced or omitted.

The power-on timer 136 calculates the time elapsed since the power-on of the medical stereoscopic observation device. Additionally, when a certain amount of time elapses after power-on, the power-on timer 136 notifies the switching control section 133 of the elapse of time.

In the synchronization signal switching section 14a, the switching control section 133 does not conduct the control of the switching-related operation of the selector 134 immediately after power-on, and instead starts the control of the switching-related operation of the selector 134 after receiving a notification from the power-on timer 136.

According to a configuration like the above, in the synchronization signal switching section 14a, immediately after power-on, switching by the selector 134 is restrained irrespectively of the supply state of each of the main and sub synchronization signals, and the main synchronization signal is supplied to the first imaging section 11a, for example. Subsequently, after the elapse of a certain time, the operation related to switching the synchronization signal to be supplied to the first imaging section 11a according to the supply state of each of the main and sub synchronization signals is started. According to such a configuration, the synchronization signal switching section 14a illustrated in FIG. 6 is able to stabilize the operation related to capturing an image of the subject with the first imaging section 11a immediately after power-on.

(Modification 1-2)

Figure 7:
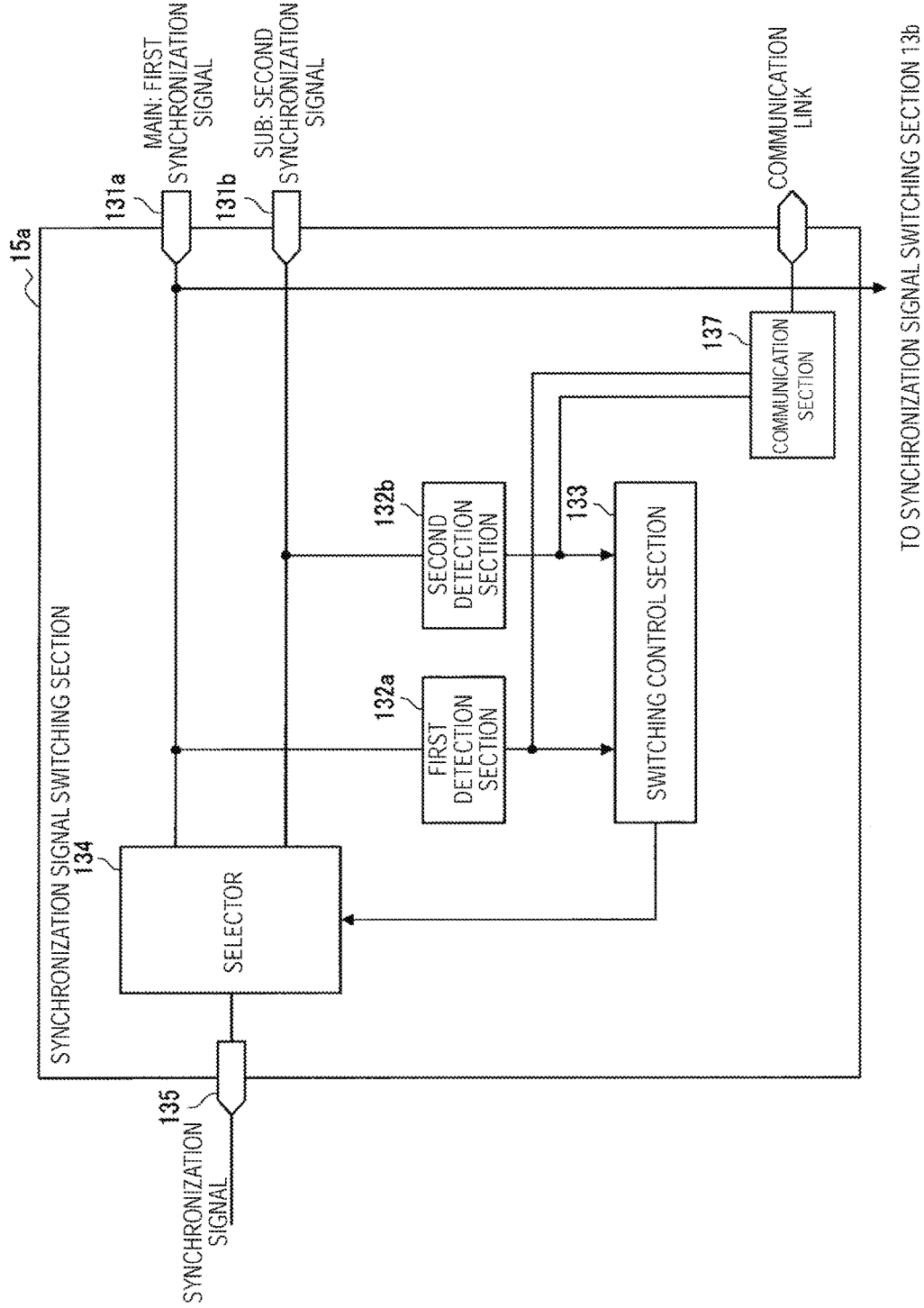
FIG. 7 is an explanatory diagram for explaining another example of a medical stereoscopic observation device according to Modification 1-2.

Next, another modification of the synchronization signal switching section will be described with reference to FIG. 7. For example, FIG. 7 is an explanatory diagram for explaining another example of a medical stereoscopic observation device according to Modification 1-2, and is a block diagram illustrating a functional configuration of another modification of the synchronization signal switching section. Note that the synchronization signal switching section illustrated in FIG. 7 may be designated the "synchronization signal switching section 15a" in some cases, to distinguish from the synchronization signal switching sections 13a and 14a discussed above.

As illustrated in FIG. 7, the synchronization signal switching section 15a differs from the synchronization signal switching section 13a discussed earlier with reference to FIG. 4 by being provided with a communication section 137. Accordingly, the following description will focus on the portion of the configuration of the synchronization signal switching section 15a that is different from the synchronization signal switching section 13a discussed earlier, while a detailed description of the portion that is substantially similar to the synchronization signal switching section 13a will be reduced or omitted.

The communication section 137 reports the synchronization signal detection result from each of the first detection section 132a and the second detection section 132b to another external device different from the imaging unit 10 via a certain communication link (network). Note that the mode of the communication link is not particularly limited, and may be a wired communication link or a wireless communication link, for example. Also, obviously the configuration of the communication section 137 may be different depending on the mode of the communication link. For example, in a case in which the detection results are reported via a wireless communication link, the communication section 137 may be equipped with components such as an RF circuit and a baseband processor.

According to such a configuration, for example, in a case of entering circumstances in which the input of the main synchronization signal (first synchronization signal) is not detected because of damage to the transmission cable or the like (that is, circumstances in which there is a break in the supply of the main synchronization signal), synchronization signal switching section 15a is able to report the same content to an external device. Consequently, the external device is able to inform the user about the malfunction in the transmission cable or the like, for example.

In addition, the external device to which is reported the synchronization signal detection result from each of the first detection section 132a and the second detection section 132b may also be the image processing device 20. By taking such a configuration, for example, when the sub synchronization signal (second synchronization signal) is supplied to the first imaging section 11a instead of the main synchronization signal (first synchronization signal), the image processing device 20 is able to recognize the same content based on the report from the synchronization signal switching section 15a. Consequently, when the first imaging section 11a captures an image on the basis of the sub synchronization signal, the image processing device 20 is also able to perform certain correction processing on the image captured by the first imaging section 11a.

(Modification 1-3)

Figure 8:
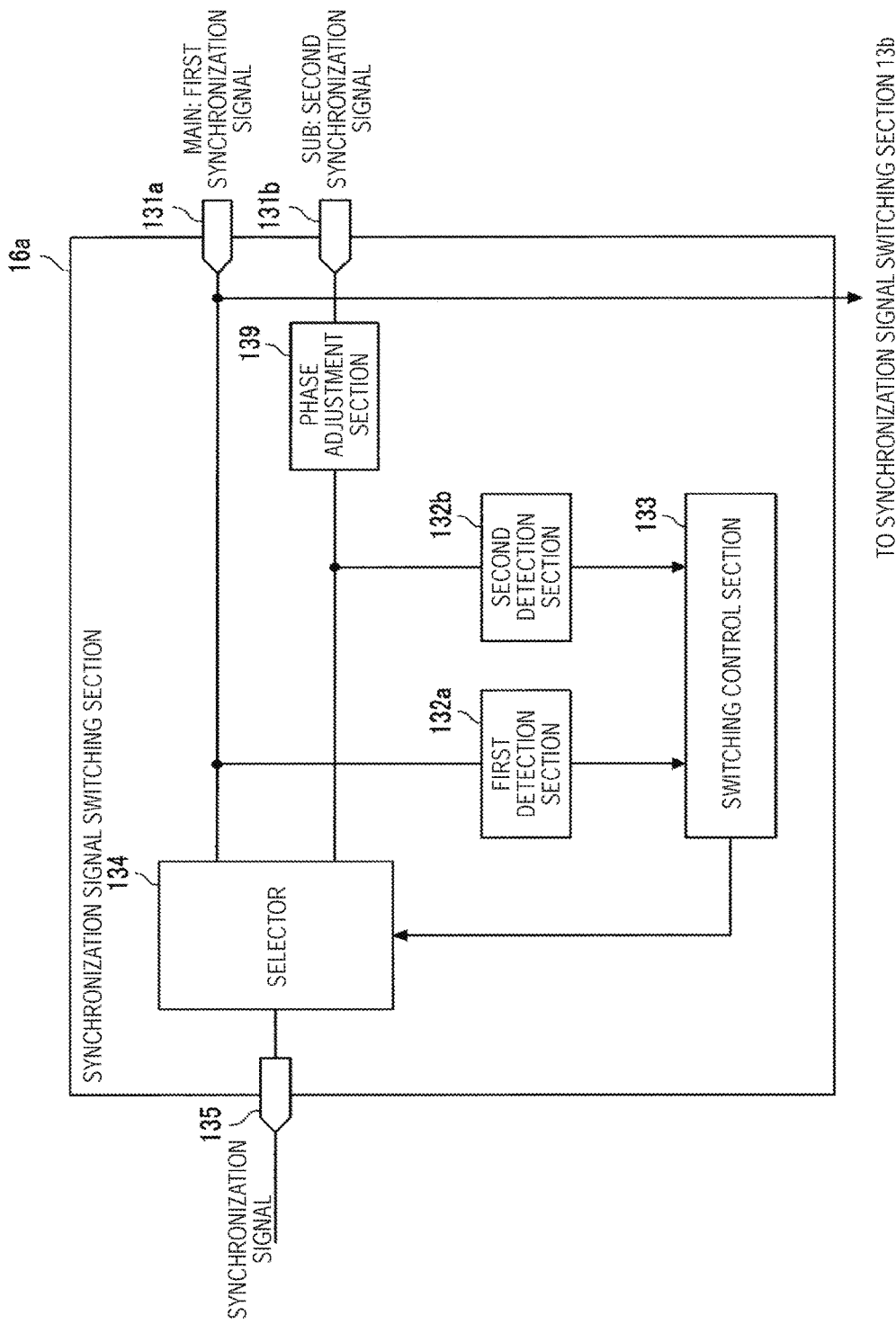
FIG. 8 is an explanatory diagram for explaining another example of a medical stereoscopic observation device according to Modification 1-3.

Next, another modification of the synchronization signal switching section will be described with reference to FIG. 8. For example, FIG. 8 is an explanatory diagram for explaining another example of a medical stereoscopic observation device according to Modification 1-3, and is a block diagram illustrating a functional configuration of another modification of the synchronization signal switching section. Note that the synchronization signal switching section illustrated in FIG. 8 may be designated the "synchronization signal switching section 16a" in some cases, to distinguish from the synchronization signal switching sections 13a, 14a, and 15a discussed above.

As illustrated in FIG. 8, the synchronization signal switching section 16a differs from the synchronization signal switching section 13a discussed earlier with reference to FIG. 4 by being provided with a phase adjustment section 139. Accordingly, the following description will focus on the portion of the configuration of the synchronization signal switching section 16a that is different from the synchronization signal switching section 13a discussed earlier, while a detailed description of the portion that is substantially similar to the synchronization signal switching section 13a will be reduced or omitted.

Specifically, the first synchronization signal supplied as the main synchronization signal to the first imaging section 11a and the second synchronization signal supplied as the main synchronization signal to the second imaging section 11b are not necessarily synchronized with each other, and may be controlled to have a phase difference in some cases. In light of such circumstances, in the synchronization signal switching section 16a illustrated in FIG. 8, the sub synchronization signal (second synchronization signal) input from the input terminal 131b is input into the phase adjustment section 139, and the phase thereof is adjusted by the phase adjustment section 139. Subsequently, the sub synchronization signal with the phase adjusted by the phase adjustment section 139 is input into the selector 134 and the second detection section 132b.

According to such a configuration, even under circumstances in which the second synchronization signal is supplied to the first imaging section 11a instead of the first synchronization signal, the synchronization signal switching section 16a is able to control the operation of the first imaging section 11a after first absorbing the phase difference between the first synchronization signal and the second synchronization signal.

The above thus references FIGS. 6 to 8 to describe modifications to the synchronization signal switching section 13 described with reference to FIG. 4 as Modification 1. Note that it is also possible to combine two or more modifications among Modifications 1-1 to 1-3 described above. As a specific example, in the case of combining Modification 1-1 and Modification 1-2, for example, the synchronization signal switching section 14a according to Modification 1-1 may be provided with the communication section 137 in the synchronization signal switching section 15a according to Modification 1-2. Similarly, in the case of combining Modification 1-1 and Modification 1-3, for example, the synchronization signal switching section 14a according to Modification 1-1 may be provided with the phase adjustment section 139 in the synchronization signal switching section 16a according to Modification 1-3.

<5.2. Modification 2: Control Signal Switching>

Next, a medical stereoscopic observation device according to Modification 2 will be described. In the foregoing embodiment and modifications, for example, the first imaging section is provided with respective transmission channels so that the first synchronization signal associated with the first imaging section, and the second synchronization signal associated with the second imaging section, are supplied. Additionally, the synchronization signal to supply to the first imaging section is configured to be switched between the first synchronization signal and the second synchronization signal, depending on the state of the transmission channel that supplies the first synchronization signal. On the other hand, the control signals supplied from the image processing device 20 to the first imaging section and the second imaging section via the transmission cable are not necessarily limited to only control signals for controlling timings related to the capturing of images, like the synchronization signals discussed above. As a specific example, control signals for controlling settings related to the operation of the first imaging section and the second imaging section, such as settings for the shutter speed and various operating modes, are also possible. Accordingly, as Modification 2, an example will be described for a case in which a control signal for controlling various settings for the first imaging section is switched between a first control signal associated with the first imaging section, and a second control signal associated with the second imaging section.

Figure 9:
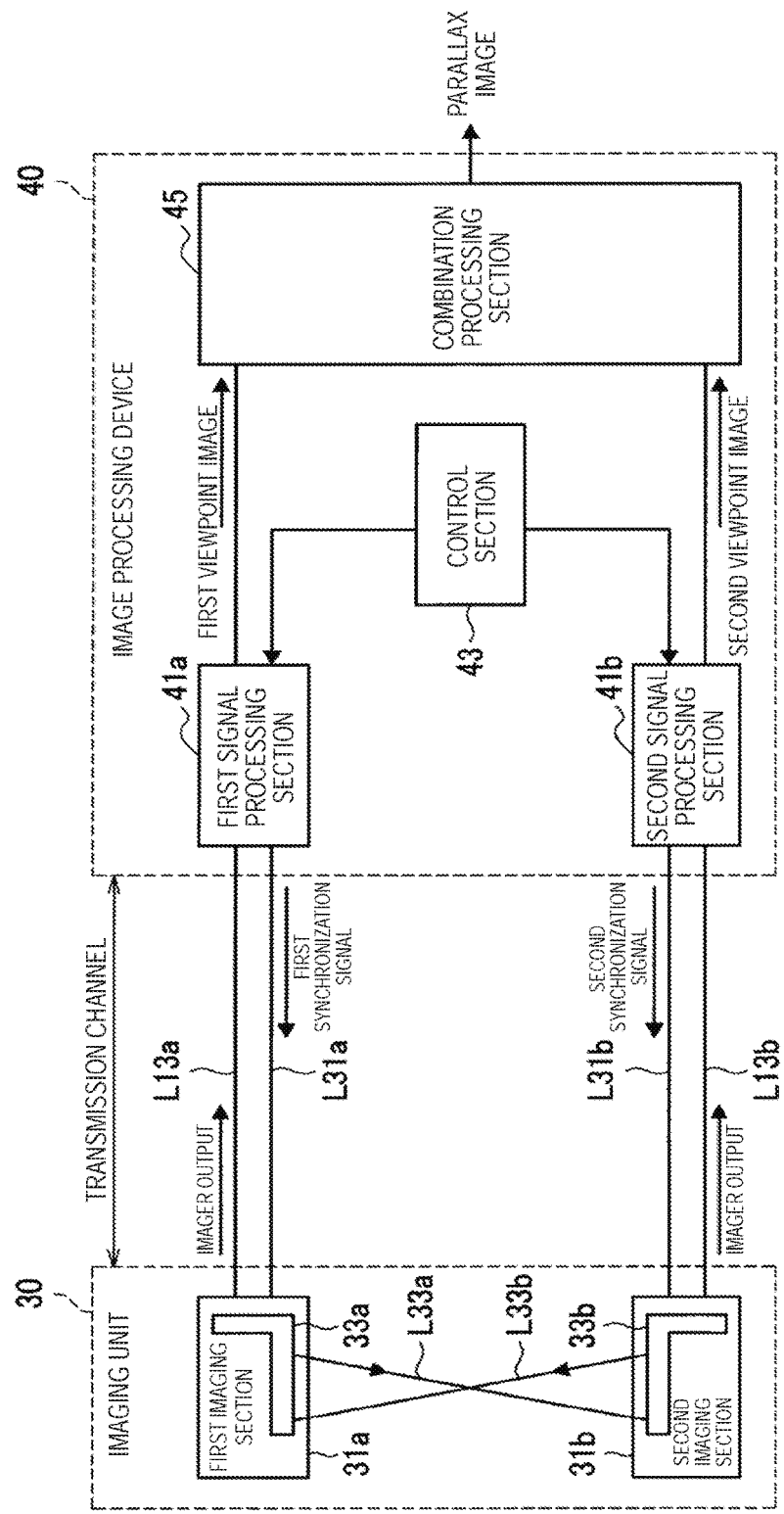
FIG. 9 is a block diagram illustrating an example of a functional configuration of a medical stereoscopic observation device according to Modification 2.

For example, FIG. 9 is a block diagram illustrating an example of a functional configuration of a medical stereoscopic observation device according to Modification 2. As illustrated in FIG. 9, the medical stereoscopic observation device 2 according to Modification 2 includes an imaging unit 30 and an image processing device 40. The imaging unit 30 corresponds to the imaging unit 10 in the medical stereoscopic observation device 1 discussed earlier with reference to FIG. 3, and includes a first imaging section 31a and a second imaging section 31b. In other words, the first imaging section 31a and the second imaging section 31b correspond to the first imaging section 11a and the second imaging section 11b in the imaging unit 10. Also, the image processing device 40 corresponds to the image processing device 20 in the medical stereoscopic observation device 1. Note that the following description of the functional configuration of the medical stereoscopic observation device 2 according to Modification 2 will focus on the portion that is different from the medical stereoscopic observation device 1 according to the foregoing embodiment, while a detailed description of the portion that is substantially similar to the medical stereoscopic observation device 1 will be reduced or omitted.

First, the description will focus on the configuration of the image processing device 40. As illustrated in FIG. 9, the image processing device 40 includes a first signal processing section 41a, a second signal processing section 41b, a control section 43, and a combination processing section 45. Note that the first signal processing section 41a, the second signal processing section 41b, and the combination processing section 45 correspond to the first signal processing section 21a, the second signal processing section 21b, and the combination processing section 25 in the medical stereoscopic observation device 1 discussed earlier.

The control section 43 is made up of any of various types of processors or microcontrollers, such as a central processing unit (CPU) or a digital signal processor (DSP), for example, and controls the operation of the image processing device 40 (that is, the operation of the first imaging section 31a and the second imaging section 31b) connected to the image processing device 40 via the transmission cable. The control section 43, in response to an instruction from the user input via an input device not illustrated, for example, outputs a first control signal for controlling various settings of the first imaging section 31a to the first signal processing section 41a, and outputs a second control signal for controlling various settings of the second imaging section 31b to the second signal processing section 41b.

The first signal processing section 41a receives the output of the first control signal from the control section 43, and supplies the first control signal to the first imaging section 31a via a transmission channel L31a provided in the transmission cable. Similarly, the second signal processing section 41b receives the output of the second control signal from the control section 43, and supplies the second control signal to the second imaging section 31b via a transmission channel L31b provided in the transmission cable. In the medical stereoscopic observation device 2 according to the present modification, the control section 43 outputs control signals for controlling settings related to the operation of a corresponding imaging section (namely, the first control signal and the second control signal) to the first signal processing section 41a and the second signal processing section 41b. Consequently, the control section 43 is able to collectively control the first imaging section 31a and the second imaging section 31b.

Next, the description will focus on the configuration of the imaging unit 30. In the imaging unit 30, each of the first imaging section 31a and the second imaging section 31b includes a control signal switching section 33. Note that in the following description, when distinguishing between the control signal switching sections 33 of the first imaging section 31a and the second imaging section 31b, respectively, the first imaging section 31a side will be designated the "control signal switching section 33a", while the second imaging section 31b side will be designated the "control signal switching section 33b". The control signal switching sections 33a and 33b are interconnected via transmission channels L33a and L33b. Note that the transmission channels L33a and L33b may apply a configuration similar to the transmission channels L15a and L15b in the imaging unit 10 according to the foregoing embodiment.

The control signal switching section 33a is supplied with the first control signal associated with the first imaging section 31a from the image processing device 40 via the transmission channel L31a provided inside the transmission cable. Also, the first control signal supplied via the transmission channel L31a is split, and one part of the split first control signal is also supplied to the control signal switching section 33b via the transmission channel L33a. Similarly, the control signal switching section 33b is supplied with the second control signal associated with the second imaging section 31b from the image processing device 40 via the transmission channel L31b provided inside the transmission cable. Also, the second control signal supplied via the transmission channel L31b is split, and one part of the split second control signal is also supplied to the control signal switching section 33a via the transmission channel L33b. According to a configuration like the above, it becomes possible to supply each of the control signal switching sections 33a and 33b with both the first control signal and the second control signal via mutually different transmission channels.

Subsequently, the control signal switching section 33a switches the control signal to supply to the first imaging section 31a between the first control signal and the second control signal, in accordance with the state of the transmission channel L31a provided inside the transmission cable (in other words, the supply state of the first control signal). Similarly, the control signal switching section 33b switches the control signal to supply to the second imaging section 31b between the first control signal and the second control signal, in accordance with the state of the transmission channel L31b provided inside the transmission cable (in other words, the supply state of the second control signal).

Figure 10:
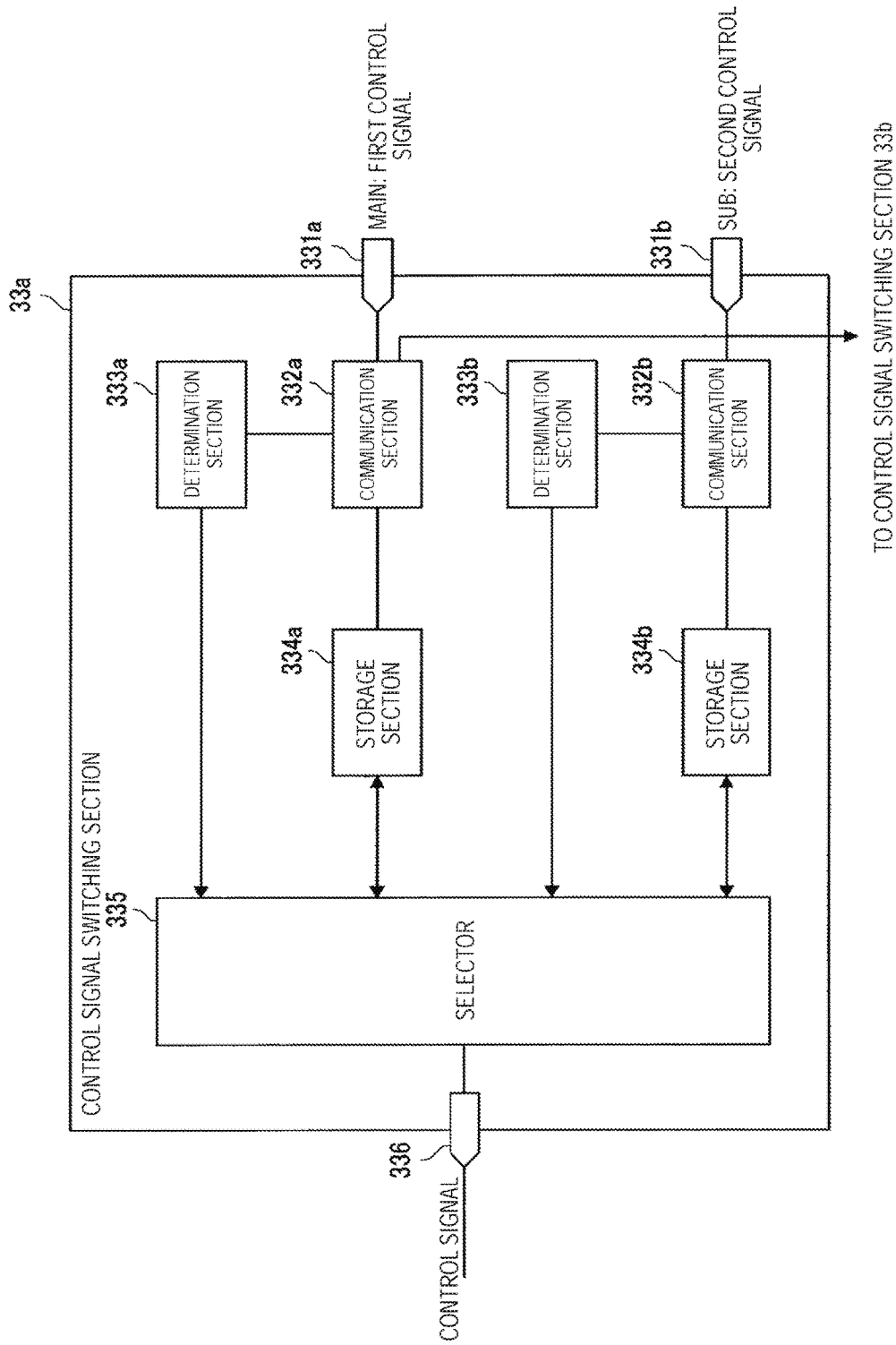
FIG. 10 is a block diagram illustrating an example of a functional configuration of a control signal switching section according to Modification 2.

At this point, a more detailed configuration of the control signal switching section 33 will be described with reference to FIG. 10. FIG. 10 is a block diagram illustrating an example of a functional configuration of the control signal switching section 33 according to Modification 2. Note that the control signal switching sections 33a and 33b have a similar configuration, except for differences in the supply source of the first control signal and the second control signal, and the supply destination of the control signal. For this reason, the following description will focus on the control signal switching section 33a side, while a detailed description of the control signal switching section 33b will be reduced or omitted.

As illustrated in FIG. 10, the control signal switching section 33a includes input terminals 331a and 331b, communication sections 332a and 332b, determination sections 333a and 333b, storage sections 334a and 334b, a selector 335, and an output terminal 336. The input terminal 331a is an input terminal that accepts the input of a control signal supplied via a transmission channel provided inside the transmission cable as a main control signal. Also, the input terminal 331b is an input terminal that accepts the input of the control signal supplied from the other control signal switching section 33 side as a sub control signal. In other words, in the control signal switching section 33a, the first control signal supplied via the transmission channel L31a illustrated in FIG. 9 is input into the input terminal 331a. Meanwhile, the second control signal supplied via the transmission channel L33b is input into the input terminal 331b.

The communication section 332a is configured to receive the first control signal from the image processing device 40 via the transmission channel L31a inside the transmission cable. In other words, the first control signal input into the input terminal 331a is received by the communication section 332a. The communication section 332a stores the received first control signal in the storage section 334a. The storage section 334a is made up of a storage medium such as random access memory (RAM), for example, and temporarily (or permanently) holds the first control signal (or information indicating the first control signal). Additionally, the communication section 332a may also transmit part of the first control signal split by a splitter or the like to the control signal switching section 33b side via the transmission channel L33a illustrated in FIG. 9. Also, the communication section 332a monitors the state of communication via the transmission channel L31a inside the transmission cable, and reports the monitoring result to the determination section 333a.

The communication section 332b is configured to receive the second control signal from the control signal switching section 33b via the transmission channel L33b. In other words, the second control signal input into the input terminal 331b is received by the communication section 332b. The communication section 332b stores the received second control signal in the storage section 334b. The storage section 334b has a configuration similar to the storage section 334a discussed above, and temporarily (or permanently) holds the second control signal (or information indicating the second control signal). Also, the communication section 332b monitors the state of communication via the transmission channel L33b, and reports the monitoring result to the determination section 333b.

The determination section 333a receives the report of the monitoring result of the state of communication via the transmission channel L31a inside the transmission cable from the communication section 332a, and based on the report, determines whether or not the reception of the first control signal via the transmission channel L31a is successful. Subsequently, the determination section 333a outputs the determination result to the selector 335. According to such a configuration, it becomes possible to control the switching-related operation of the selector 335 based on the determination result of the determination section 333a.

Meanwhile, the determination section 333b receives the report of the monitoring result of the state of communication via the transmission channel L33b from the communication section 332b, and based on the report, determines whether or not the reception of the second control signal via the transmission channel L33b is successful. Subsequently, the determination section 333b outputs information indicating the determination result to the selector 335. According to such a configuration, it becomes possible to control the switching-related operation of the selector 335 based on the determination result of the determination section 333b.

The selector 335 acquires information indicating the determination result from each of the determination section 333a and the determination section 333b, and based on the acquired information, recognizes the reception status of each of the first control signal and the second control signal (in other words, whether or not the reception of each control signal is successful). Subsequently, depending on the recognition result of the reception status of each control signal, the selector 335 selectively reads out either the main control signal stored in the storage section 334a (that is, the first control signal) or the sub control signal stored in the storage section 334b (that is, the second control signal), and supplies the read-out control signal to the first imaging section 31a.

For example, if the selector 335 recognizes that the reception of the main control signal (that is, the first control signal) is successful based on the determination result from the determination section 333a, the selector 335 reads out the main control signal stored in the storage section 334a, and supplies the read-out control signal to the first imaging section 31a. As another example, if there is a break in the transmission channel L31a because of damage to the transmission cable or the like, and the reception of the first control signal fails, the selector 335 is able to recognize the failure in the reception of the first control signal based on the determination result from the determination section 333a. In this case, the selector 335 may read out the sub control signal stored in the storage section 334b (that is, the second control signal), and supply the read-out control signal to the first imaging section 31a. Obviously, the above are merely examples, and the configuration is not particularly limited, insofar as the selector 335 is able to switch the control signal to supply to the first imaging section 31a between the main control signal and the sub control signal based on the respective determination results from the determination sections 333a and 333b.

Based on a configuration like the above, the control signal switching section 33a recognizes the acquisition status of each of the main control signal and the sub control signal, and in accordance with the recognition result, switches the control signal to be supplied to the first imaging section 31a between the main control signal and the sub control signal. According to such a configuration, even under circumstances in which acquiring the main control signal becomes difficult, for example, the control signal switching section 33a is still able to supply the sub control signal to the first imaging section 31a instead of the main control signal. For this reason, even if there is a break in the transmission channel L31a illustrated in FIG. 9 because of damage to the transmission cable or the like, and supplying the first control signal to the first imaging section 31a becomes difficult, for example, supplying the second control signal makes it possible to continue capturing images with the first imaging section 31a.

The above thus references FIGS. 9 and 10 to describe, as Modification 2, an example for a case in which a control signal for controlling various settings for the first imaging section is switched between a first control signal associated with the first imaging section, and a second control signal associated with the second imaging section. Note that the medical stereoscopic observation device 2 according to Modification 2 discussed above may also be combined with the medical stereoscopic observation device 1 according to the foregoing embodiment. In this case, for example, it is sufficient to provide the medical stereoscopic observation device 1 with least part of the configuration of the medical stereoscopic observation device 2 (for example, the configuration for transmitting the first and second control signals, and the configuration related to control signal switching), or with functions corresponding to such a configuration.

<5.3. Modification 3: Switching Channel for Acquiring Information from Each Imaging Unit>

Next, a medical stereoscopic observation device according to Modification 3 will be described. The embodiment and modifications discussed above describe an example of a case in which control signals are supplied from an image processing device to respective imaging sections via mutually different transmission channels, while on the imaging section side, the control signal to use for actual control is selectively switched among the supplied control signals, in accordance with the state of the transmission channel. In contrast, Modification 3 describes an example of a case in which the image processing device receives the feedback of information from the imaging sections via mutually different transmission channels, and the information to use for actual control among the feedback information is selectively switched among the feedback information, in accordance with the state of the transmission channel.

Figure 11:
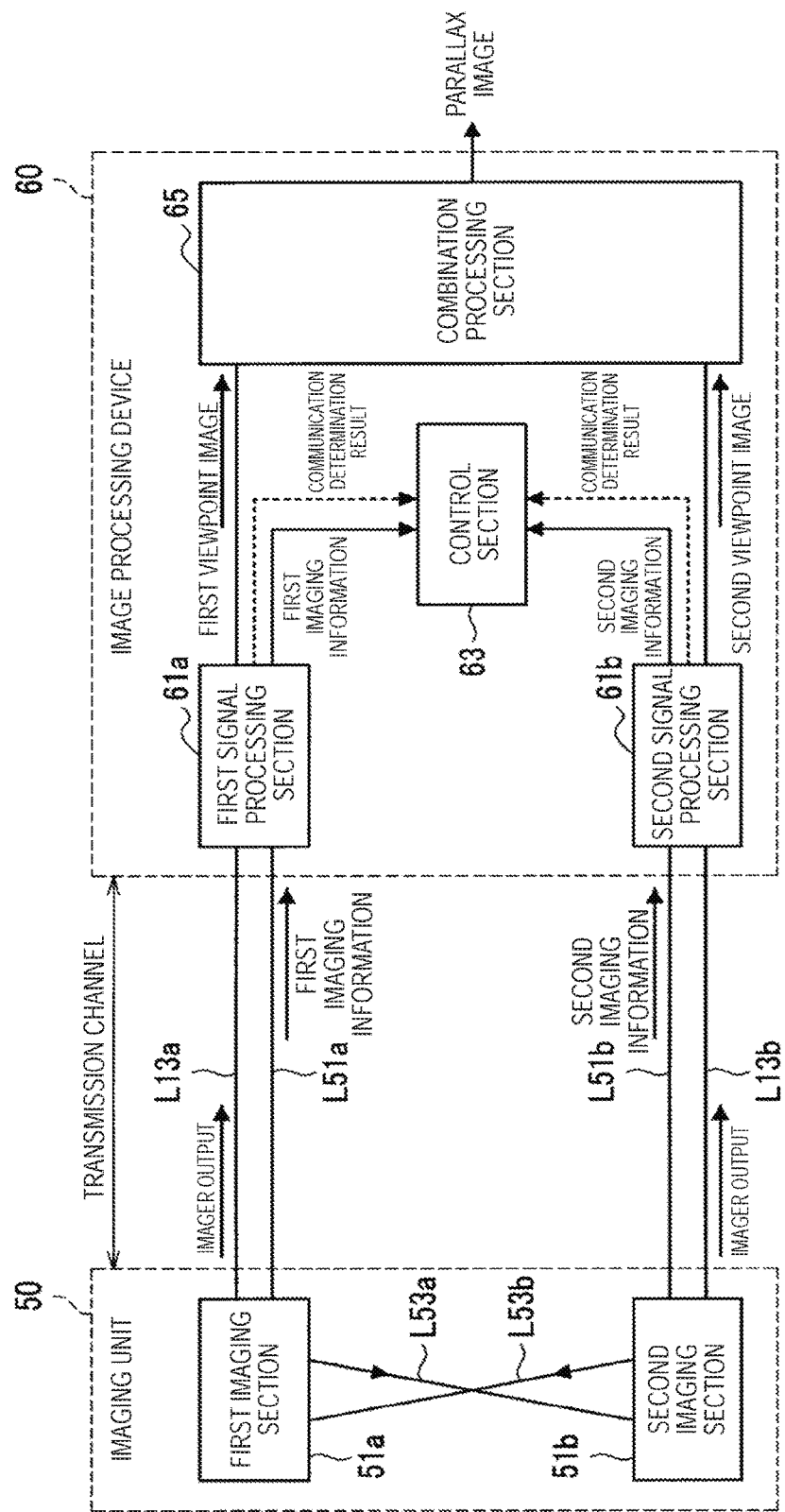
FIG. 11 is a block diagram illustrating an example of a functional configuration of a medical stereoscopic observation device according to Modification 3.

For example, FIG. 11 is a block diagram illustrating an example of a functional configuration of a medical stereoscopic observation device according to Modification 3. As illustrated in FIG. 11, the medical stereoscopic observation device 3 according to Modification 3 includes an imaging unit 50 and an image processing device 60. The imaging unit 50 corresponds to the imaging unit 10 in the medical stereoscopic observation device 1 discussed earlier with reference to FIG. 3, for example, and includes a first imaging section 51a and a second imaging section 51b. In other words, the first imaging section 51a and the second imaging section 51b correspond to the first imaging section 11a and the second imaging section 11b in the imaging unit 10. Also, the image processing device 60 corresponds to the image processing device 20 in the medical stereoscopic observation device 1. Note that the following description of the functional configuration of the medical stereoscopic observation device 3 according to Modification 3 will focus on the portion that is different from the medical stereoscopic observation device 1 according to the foregoing embodiment, while a detailed description of the portion that is substantially similar to the medical stereoscopic observation device 1 will be reduced or omitted. Also, in the following description, information that is fed back from the first imaging section 51a to the image processing device 60 is also designated "first imaging information", while information that is fed back from the second imaging section 51b to the image processing device 60 is also designated "second imaging information".

First, the description will focus on the configuration of the imaging unit 50. As illustrated in FIG. 11, in the imaging unit 50, the first imaging section 51a and the second imaging section 51b are interconnected via transmission channels L53a and L53b. Note that the transmission channels L53a and L53b may apply a configuration similar to the transmission channels L15a and L15b in the imaging unit 10 according to the foregoing embodiment.

The first imaging section 51a transmits at least part of the first imaging information fed back to the image processing device 60 to the second imaging section 51b via the transmission channel L53a. Also, the first imaging section 51a acquires at least part of the second imaging information that the second imaging section 51b feeds back to the image processing device 60 from the second imaging section 51b via the transmission channel L53b. Subsequently, the first imaging section 51a transmits the first imaging information and the information acquired from the second imaging section 51b (that is, at least part of the second imaging information) to the image processing device 60 via a transmission channel L51a provided inside the transmission cable.

Similarly, the second imaging section 51b transmits at least part of the second imaging information fed back to the image processing device 60 to the first imaging section 51a via the transmission channel L53b. Also, the second imaging section 51b acquires at least part of the first imaging information that the first imaging section 51b feeds back to the image processing device 60 from the first imaging section 51a via the transmission channel L53a. Subsequently, the second imaging section 51b transmits the second imaging information and the information acquired from the first imaging section 51a (that is, at least part of the first imaging information) to the image processing device 60 via a transmission channel L51b provided inside the transmission cable.

Next, the description will focus on the configuration of the image processing device 60. As illustrated in FIG. 11, the image processing device 60 includes a first signal processing section 61a, a second signal processing section 61b, a control section 63, and a combination processing section 65. Note that the first signal processing section 61a, the second signal processing section 61b, and the combination processing section 65 correspond to the first signal processing section 21a, the second signal processing section 21b, and the combination processing section 25 in the medical stereoscopic observation device 1 discussed earlier.

The first signal processing section 61a acquires the first imaging information and at least part of the second imaging information from the first imaging section 51a via the transmission channel L51a provided inside the transmission cable, and outputs the acquired information to the control section 63. Also, the first signal processing section 61a monitors communication with the first imaging section 51a via the transmission channel L51a, and reports the monitoring result to the control section 63.

Additionally, the second signal processing section 61b acquires the second imaging information and at least part of the first imaging information from the second imaging section 51b via the transmission channel L51b provided inside the transmission cable, and outputs the acquired information to the control section 63. Also, the second signal processing section 61b monitors communication with the second imaging section 51b via the transmission channel L51b, and reports the monitoring result to the control section 63.

The control section 63 acquires the first imaging information and at least part of the second imaging information from the first signal processing section 61a. Also, the control section 63 acquires the second imaging information and at least part of the first imaging information from the second signal processing section 61b.

In addition, the control section 63 receives a report about the monitoring result of communication with the first imaging section 51a via the transmission channel L51a from the first signal processing section 61a, and based on this report, determines whether or not the reception of information via the transmission channel L51a is successful. Similarly, the control section 63 receives a report about the monitoring result of communication with the second imaging section 51b via the transmission channel L51b from the second signal processing section 61b, and based on this report, determines whether or not the reception of information via the transmission channel L51b is successful.

Based on a configuration like the above, the control section 63 switches the acquisition route of the information fed back from each of the first imaging section 51a and the second imaging section 51b between the transmission channels L51a and L51b, based on the respective monitoring results of communication via the transmission channels L51a and L51b.

As a specific example, when communication via the transmission channel L51a is operating normally, the control section 63 adopts the first imaging information acquired by the first signal processing section 61a as feedback from the first imaging section 51a. In this case, the control section 63 may also discard the at least part of the first imaging information acquired by the second signal processing section 61b.

On the other hand, if communication via the transmission channel L51a fails, it may become difficult for the first signal processing section 61a to acquire the first imaging information via the transmission channel L51a. In this case, the control section 63 adopts the at least part of the first imaging information acquired by the second signal processing section 61b as feedback from the first imaging section 51a.

Similarly, when communication via the transmission channel L51b is operating normally, the control section 63 adopts the second imaging information acquired by the second signal processing section 61b as feedback from the second imaging section 51b. In this case, the control section 63 may also discard the at least part of the second imaging information acquired by the first signal processing section 61a.

Also, if communication via the transmission channel L51b fails, it may become difficult for the second signal processing section 61b to acquire the second imaging information via the transmission channel L51b. For this reason, the control section 63 adopts the at least part of the second imaging information acquired by the first signal processing section 61a as feedback from the second imaging section 51b.

According to a configuration like the above, for example, even if there is a break in the transmission channel L51a because of damage to the transmission cable or the like, and it becomes difficult to receive feedback directly from the first imaging section 51a, the image processing device 60 is still able to acquire at least part of the information from the second imaging section 51b. Consequently, for example, based on the information acquired from the second imaging section 51b, the image processing device 60 is able to continue processing related to the first imaging section 51a (in other words, processing based on feedback from the first imaging section Ma). Additionally, depending on the route by which feedback from the first imaging section 51a (that is, the first imaging information) is acquired, the image processing device 60 may also change the content of processing based on such feedback (for example, the processing of an image captured by the first imaging section 51a). Obviously, the above also applies similarly to the feedback from the second imaging section 51b.

The above thus references FIG. 11 to describe, as Modification 3, an example of a case in which the image processing device receives the feedback of information from the imaging sections via mutually different transmission channels, and the information to use for actual control among the feedback information is selectively switched among the feedback information, in accordance with the state of the transmission channel. Note that the medical stereoscopic observation device 3 according to Modification 3 discussed above may also be combined with at least one of the medical stereoscopic observation device 1 according to the foregoing embodiment and the medical stereoscopic observation device 2 according to Modification 1. For example, in the case of combining the medical stereoscopic observation devices 1 and 3, for example, it is sufficient to provide the medical stereoscopic observation device 1 with at least part of the configuration of the medical stereoscopic observation device 3 (for example, the configuration for transmitting the first and second imaging information, and the configuration related to switching the route for acquiring the respective imaging information), or with functions corresponding to such a configuration.

6. Applied Examples

The foregoing describes an example of applying a medical stereoscopic observation device according to the present embodiment to a surgical video microscope device. However, the application of a medical stereoscopic observation device according to the present embodiment is not necessarily limited only to a surgical video microscope device. Accordingly, applied examples of a medical stereoscopic observation device according to the present embodiment are described below.

<6.1. First Applied Example: Rigid Endoscopic Device>

Figure 12:
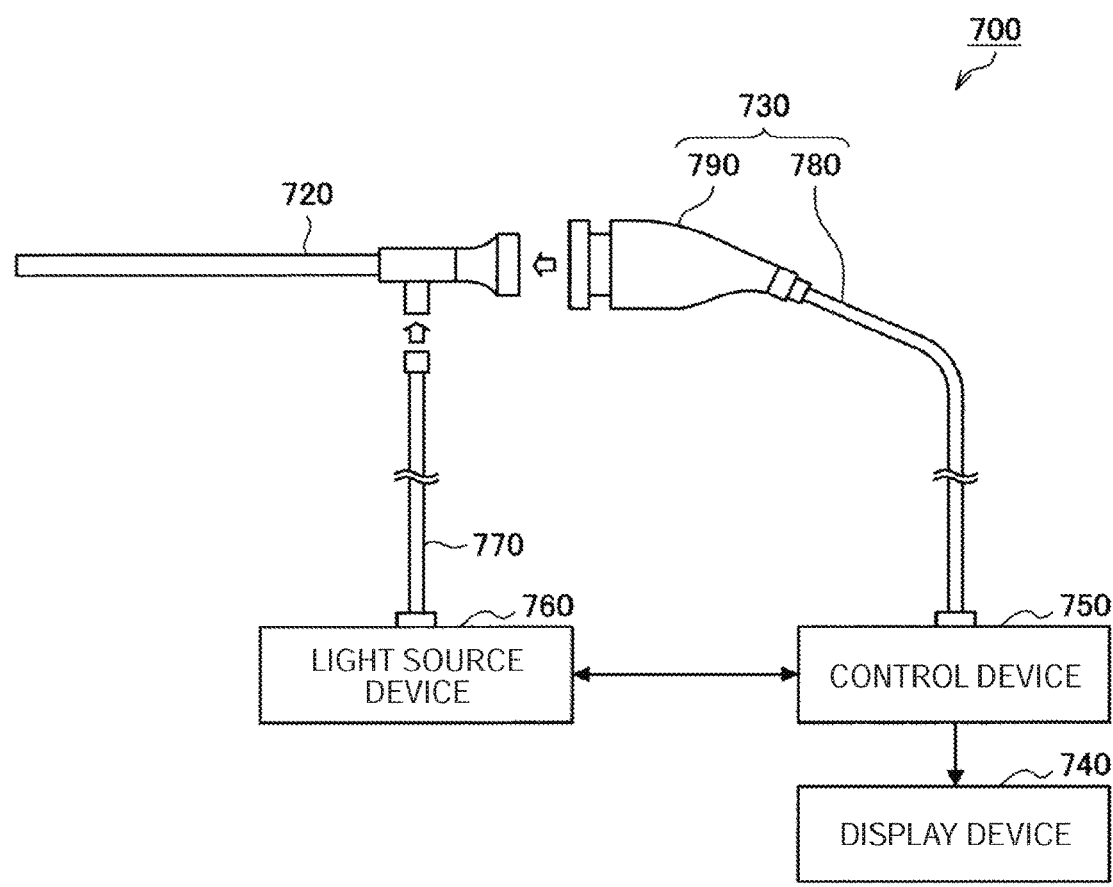
FIG. 12 is an explanatory diagram for explaining a first applied example of a medical stereoscopic observation device according to an embodiment.
Figure 13:
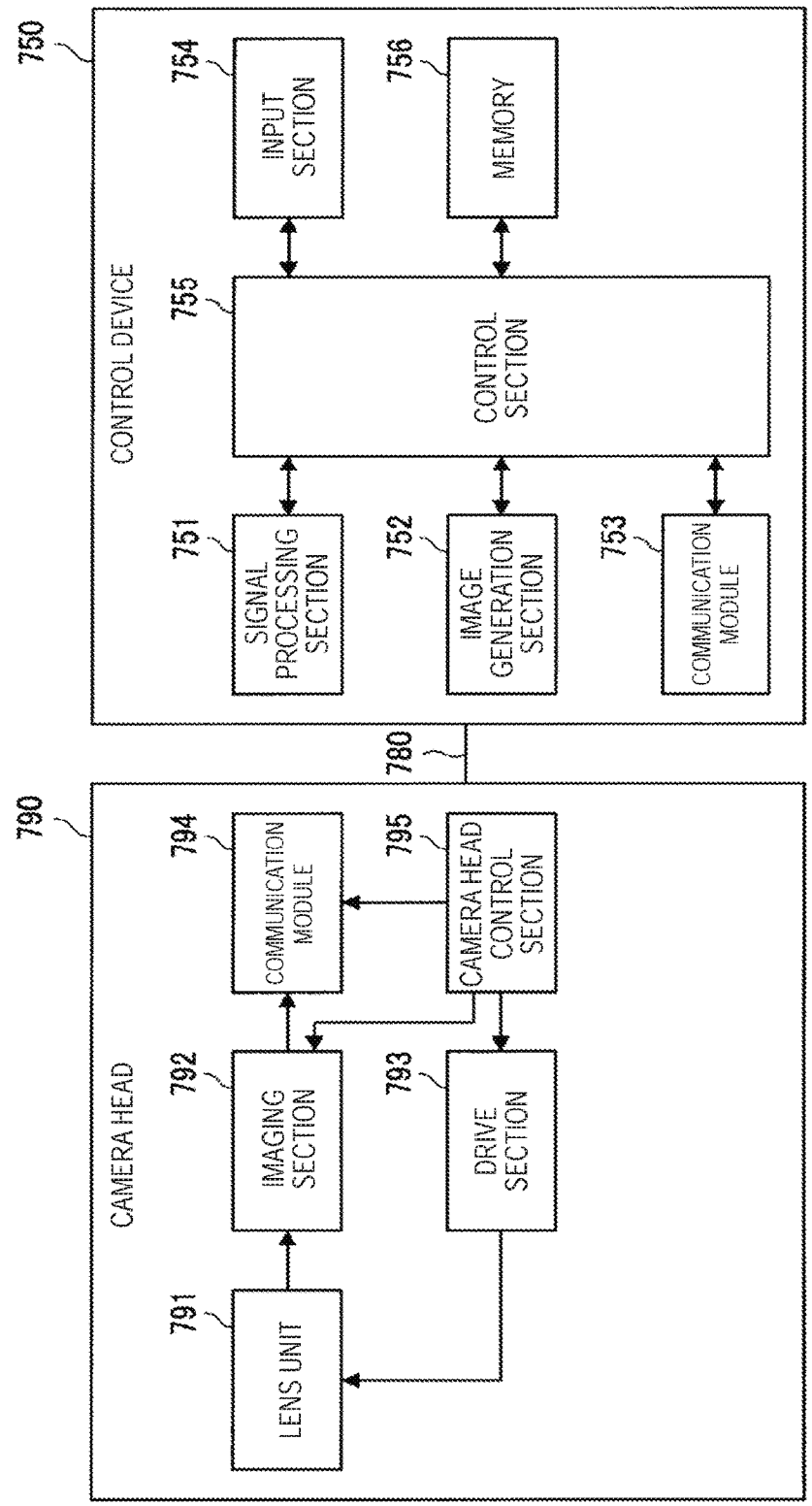
FIG. 13 is an explanatory diagram for explaining a first applied example of a medical stereoscopic observation device according to an embodiment.

First, as a first applied example of the present embodiment, FIGS. 12 and 13 will be referenced to describe an example of a case of applying a medical stereoscopic observation device according to the present embodiment to what is called a rigid endoscopic device. For example, FIG. 12 is an explanatory diagram for explaining a first applied example of a medical stereoscopic observation device according to the present embodiment, and illustrates an example of a schematic configuration of a rigid endoscopic device. The endoscopic device 700 is a device used in the medical field that enables one to observe a photographic subject of the interior (the inside of the body) of a target of observation, such as a person. As illustrated in FIG. 12, the endoscopic device 700 is equipped with an endoscope 720, an imaging device 730 (medical imaging device), a display device 740, a control device 750 (image processing device), and a light source device 760, in which the imaging device 730 and the control device 750 constitute a medical image acquisition system. Note that in the present applied example, the endoscope 720 and the imaging device 730 constitute an endoscopic device using a rigid scope.

One end of a light guide 770 is connected to the endoscope 720, and the light source device 760 supplies white illuminating light for illuminating the inside of the body to the one end of the light guide 770. One end of the light guide 770 is removably connected to the light source device 760, while the other end is removably connected to the endoscope 720. Additionally, the light guide 770 transmits light supplied from the light source device 760 from the one end to the other end, thereby supplying the light to the endoscope 720.

The imaging device 730 captures a subject image from the endoscope 720, and outputs the imaging result. As illustrated in FIG. 12, the imaging device 730 is equipped with a transmission cable 780 which is a signal transmission section, and a camera head 790. In the present applied example, the medical imaging device is constituted by the transmission cable 780 and the camera head 790.

The endoscope 720 has a rigid elongated shape, and is inserted inside the body. Provided in the interior of the endoscope 720 is an optical system, which is made up of one or multiple lenses, and which condenses the light of the subject image. The endoscope 720 emits light supplied through the light guide 770 from the leading end, and irradiates the inside of the body. Additionally, the light radiated inside the body (that is, the subject image) is condensed by the optical system (lens unit 791) inside the endoscope 720.

The camera head 790 is removably connected to the base of the endoscope 720. Additionally, the camera head 790, under control by the control device 750, captures a subject image condensed by the endoscope 720, and outputs an imaging signal according to the imaging. Note that the camera head 790 corresponds to the imaging unit 10 in the medical stereoscopic observation device 1 described with reference to FIG. 3, for example.

One end of the transmission cable 780 is removably connected to the control device 750 through a connector, while the other end is removably connected to the camera head 790 through a connector. Specifically, the transmission cable 780 is a cable in which multiple electrical wires (not illustrated) are arranged inside the inner part of an outer sheath that acts as the outermost layer. The multiple electrical wires are electrical wires for transmitting the imaging signal output from the camera head 790, as well as a control signal, a synchronization signal, a clock, and power output from the control device 750 to the camera head 790, respectively.

The display device 740, under control by the control device 750, displays an image generated by the control device 750. The display device 740 preferably includes a display unit of at least 55 inches to obtain a sense of immersion more easily during observation, but is not limited thereto.

The control device 750 processes the imaging signal input from the camera head 790 through the transmission cable 780, and outputs an image signal to the display device 740. In addition, the control device 750 also centrally controls the operations of the camera head 790 and the display device 740. Note that the detailed configuration of the control device 750 will be discussed later.

Next, a configuration of the imaging device 730 and the control device 750 will be described. FIG. 13 is an explanatory diagram for explaining a first applied example of a medical stereoscopic observation device according to the present embodiment, and is a block diagram illustrating a configuration of the imaging device 730 and the control device 750. Note that in FIG. 13, the connector that allows the camera head 790 and the transmission cable 780 to be removably connected to each other is omitted from illustration.

Hereinafter, the configuration of the control device 750 and the configuration of the camera head 790 will be described in order. Note that in the following, the gist of the present disclosure is described primarily as the configuration of the control device 750. As illustrated in FIG. 13, the control device 750 is equipped with a signal processing section 751, an image generation section 752, a communication module 753, an input section 754, a control section 755, and memory 756. Note that the control device 750 may also be provided with components such as a power supply unit (not illustrated) that generates a power supply voltage for driving the control device 750 and the camera head 790 and respectively supplies the power supply voltage to each component of the control device 750, while also supplying the power supply voltage to the camera head 790 through the transmission cable 780.

The signal processing section 751 performs signal processing such as noise removal, and if necessary, A/D conversion, on the imaging signal output by the camera head 790, and outputs a digitized imaging signal (pulse signal) to the image generation section 752.

Additionally, the signal processing section 751 generates a synchronization signal for the imaging device 730 and the control device 750, and a clock. The synchronization signal for the imaging device 730 (such as a synchronization signal indicating the imaging timings of the camera head 790, for example) and the clock (a clock used for serial communication, for example) are sent to the imaging device 730 on a line not illustrated, and the imaging device 730 drives on the basis of the synchronization signal and the clock.

The image generation section 752 generates a display image signal to be displayed by the display device 740, based on the imaging signal input from the signal processing section 751. The image generation section 752 executes certain signal processing on the imaging signal to generate a display image signal that includes the subject image. Herein, the image processing may be any of various types of image processing, such as interpolation processing, color correction processing, color enhancement processing, and edge enhancement processing. The image generation section 752 outputs the generated image signal to the display device 740. Note that the image processing section 751 and the image generation section 752 correspond to the image processing device 20 in the medical stereoscopic observation device 1 described with reference to FIG. 3, for example.

The communication module 753 outputs, to the imaging device 730, a signal from the control device 750 including a control signal discussed later that is transmitted from the control section 755. The communication module 753 also outputs a signal from the imaging device 730 to the control device 750. In other words, the communication module 753 is a relay device that outputs the signals from the respective components of the control device 750 to the imaging device 730 in a collective manner, such as by parallel-serial conversion, for example, and also outputs a signal input from the imaging device 730 to the respective components of the control device 750 in a distributed manner, such as by serial-parallel conversion, for example.

The input section 754 is realized using a user interface such as a keyboard, a mouse, or a touch panel, and accepts the input of various information.

The control section 755 performs controls such as drive control of each component, including the control device 750 and the camera head 790, and input/output control of information with respect to each component. The control section 755 generates a control signal by referencing communication information data recorded in the memory 756 (such as communication format information, for example), and transmits the generated control signal to the imaging device 730 through the communication module 753. The control section 755 also outputs a control signal to the camera head 790 through the transmission cable 780.

The memory 756 is realized using semiconductor memory such as flash memory or dynamic random access memory (DRAM), and records communication information data (such as communication format information, for example). Note that the memory 756 may also record information such as various programs executed by the control section 755.

Note that the signal processing section 751 may also include an AF processing section that outputs a certain AF score value for each frame based on an input frame imaging signal, and an AF computation section that performs an AF computational process of selecting the frame or the focus lens position best suited as the focus position, based on the AF score value of each frame from the AF processing section.

Note that the signal processing section 751, the image generation section 752, the communication module 753, and the control section 755 discussed above are realized by a general-purpose processor such as a central processing unit (CPU) including internal memory (not illustrated) in which a program is recorded, or by a special-purpose processor such as any of various types of computational circuits that execute a specific function, such as an application-specific integrated circuit (ASIC). Additionally, a field-programmable gate array (FPGA; not illustrated), which is a type of programmable integrated circuit, may also be used to realize the above. Note that in the case of using an FPGA, memory storing configuration data may be provided, and the FPGA, that is, the programmable integrated circuit, may be configured according to configuration data read out from the memory.

Next, the gist of the present disclosure will be described primarily as the configuration of the camera head 790. As illustrated in FIG. 13, the camera head 790 is equipped with a lens unit 791, an imaging section 792, a drive section 793, a communication module 794, and a camera head control section 795.

The lens unit 791 is configured using one or multiple lenses, and forms a subject image condensed by the endoscope 720 onto the imaging surface of an image sensor constituting the imaging section 792. The one or multiple lenses are configured to be movable on the optical axis. Additionally, the lens unit 791 is provided with a focus mechanism that moves the one or multiple lenses to vary an optical zoom mechanism (not illustrated) that varies the angle of view, or the focus point. Note that, besides the optical zoom mechanism and the focus mechanism, the lens unit 791 may also be provided with a diaphragm mechanism, or an optical filter (for example, a filter that cuts infrared light) that may be freely inserted or removed from the optical axis.

The imaging section 792 images a subject, under control by the camera head control section 795. The imaging section 792 is configured using two image sensors, each made of a device such as a charge-coupled device (CCD) or a complementary metal-oxide-semiconductor (CMOS) that senses the light of a subject image formed by the lens unit 791 and converts the light into an electrical signal, and a prism that splits the observation light and causes the split light to be respectively incident onto the two image sensors. In the CCD case, for example, a signal processing section (not illustrated) that performs signal processing (such as A/D conversion) on the electrical signal (analog signal) from the image sensor and outputs an imaging signal is implemented in a sensor chip or the like. In the CMOS case, for example, a signal processing section that performs signal processing (such as A/D conversion) on an (analog) electrical signal converted from light into an electrical signal and outputs an imaging signal is included in the image sensor. A configuration of the imaging section 792 will be discussed later.

The drive section 793 includes a driver that, under control by the camera head control section 795, causes the optical zoom mechanism and the focus mechanism to operate, and varies the angle of view and the focus position of the lens unit 791.

The communication module 794 outputs signals transmitted from the control device 750 to respective components inside the camera head 790, such as the camera head control section 795. Additionally, the communication module 794 converts information related to the current state of the camera head 790 and the like into a signal format according to a predetermined transmission scheme, and outputs the converted signal to the control device 750 through the transmission cable 780. In other words, the communication module 794 is a relay device that outputs a signal input from the control device 750 and the transmission cable 780 to respective components of the camera head 790 in a distributed manner, such as by serial-parallel conversion, for example, and also outputs signals from the respective components of the camera head 790 to the control device 750 and the transmission cable 780 in a collective manner, such as by parallel-serial conversion, for example.

The camera head control section 795 controls the operation of the camera head 790 overall, in accordance with signals such as a drive signal input through the transmission cable 780, or an instruction signal output from an operating section by a user operation on the operating section, such as a switch provided exposed on the outer face of the camera head 790. Additionally, the camera head control section 795 outputs information related to the current state of the camera head 790 to the control device 750 through the transmission cable 780.

Note that the drive section 793, the communication module 794, and the camera head control section 795 discussed above are realized by a general-purpose processor such as a central processing unit (CPU) including internal memory (not illustrated) in which a program is recorded, or by a special-purpose processor such as any of various types of computational circuits that execute a specific function, such as an application-specific integrated circuit (ASIC). Additionally, an FPGA, which is a type of programmable integrated circuit, may also be used to realize the above. Note that in the case of using an FPGA, memory storing configuration data may be provided, and the FPGA, that is, the programmable integrated circuit, may be configured in accordance with configuration data read out from the memory.

Note that the camera head 790 or the transmission cable 780 may also include a signal processing section that performs signal processing on an imaging signal generated by the communication module 794 or the imaging section 792. Additionally, based on a reference clock generated by an oscillator (not illustrated) provided inside the camera head 790, an imaging clock for driving the imaging section 792 and a driving clock for driving the drive section 793 may be generated and output to the imaging section 792 and the drive section 793, respectively. Furthermore, based on a synchronization signal input from the control device 750 through the transmission cable 780, timing signals for various processes in the imaging section 792, the drive section 793, and the camera head control section 795 may be generated and output to the imaging section 792, the drive section 793, and the camera head control section 795, respectively. Also, the camera head control section 95 may be provided not in the camera head 790, but instead in the transmission cable 780 or the control device 750.

Note that a configuration including the lens unit 791, the imaging section 792, and the drive section 793 may correspond to the first imaging section 11a or the second imaging section 11b described with reference to FIG. 3. In other words, in the case of configuring the endoscopic device 700 as a medical stereoscopic observation device according to the present embodiment, for example, it is sufficient to provide the lens unit 791, the imaging section 792, and the drive section 793 for each viewpoint (for example, for each viewpoint of the left eye and the right eye, respectively). Additionally, as illustrated in FIGS. 3 and 4, it is sufficient to provide each imaging section 792 with a switching section (for example, the synchronization signal switching section 13 or the control signal switching section 33) that switches various control signals to be supplied to the imaging section 792 provided for each viewpoint. According to such a configuration, even if there is a break in a transmission channel that supplies a control signal to one imaging section 792 among the multiple imaging sections 792 (for example, a transmission channel inside the transmission cable 780) because of damage or the like, it is still possible to supply the affected imaging section 792 with a control signal supplied to another imaging section 792 as a substitute.

The above thus references FIGS. 12 and 13 to describe, as a first applied example of the present embodiment, an example of a case of applying a medical stereoscopic observation device according to the present embodiment to what is called a rigid endoscopic device.

<6.2. Second Applied Example: Flexible Endoscopic Device>

Figure 14:
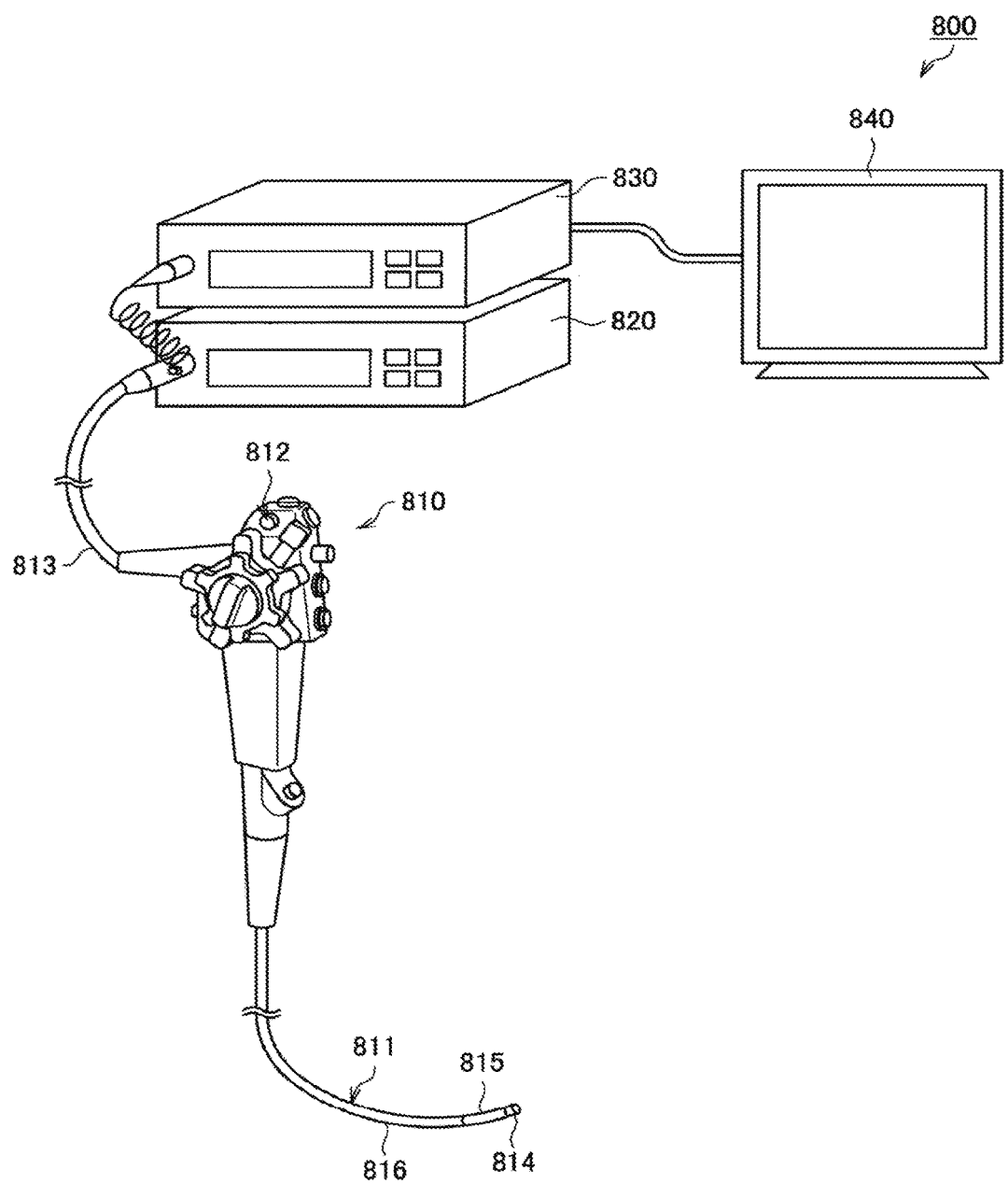
FIG. 14 is an explanatory diagram for explaining a second applied example of a medical stereoscopic observation device according to an embodiment.

Next, as a second applied example of the present embodiment, FIG. 14 will be referenced to describe an example of a case of applying a medical stereoscopic observation device according to the present embodiment to what is called a flexible endoscopic device. FIG. 14 is an explanatory diagram for explaining a second applied example of a medical stereoscopic observation device according to the present embodiment, and illustrates an example of a schematic configuration of a flexible endoscopic device.

The first applied example above describes an endoscopic device 700 using a rigid scope as the endoscope 720, but the configuration is not limited thereto, and an endoscopic device using a flexible scope as the endoscope 720 is also acceptable. The second applied example of the present embodiment describes an example of a case in which an imaging section is provided on the leading end of the insertion section of a flexible endoscope.

The endoscopic device 800 is equipped with an endoscope 810 that, by inserting an insertion section 811 inside a test subject's body, captures an internal image of an observation site and generates an electrical signal, a light source device 820 that produces illuminating light that radiates from the leading end of the endoscope 810, a control device 830 that performs certain image processing on the electrical signal acquired by the endoscope 810 and also centrally controls the operations of the endoscopic device 800 as a whole, and a display device 840 that displays an internal image processed by the a processor section. The endoscopic device 800 inserts the insertion section 811 inside the body of a test subject, such as a patient, and acquires an internal image of the inside of the test subject's body. Note that the part of the configuration of the control device 830 that executes the image processing corresponds to the image processing device 20 in the medical stereoscopic observation device 1 described with reference to FIG. 3, for example.

The endoscope 810 is equipped with a flexible insertion section 811 having an elongated shape, an operating section 812, connected to the base end side of the insertion section 811, that accepts the input of various operation signals, and a universal cord 813 which extends from the operating section 812 in a different direction from the direction in which the insertion section 811 extends, and which houses various cables that connect to the light source device 820 and the control device 830.

The insertion section 811 includes a leading end section 814 that houses an imaging section according to the present applied example, a freely bendable curved section 815 made up of multiple curve joints, and a flexible tube section 816 connected to the base end side of the curved section 815 and having a flexible elongated shape.

Note that the imaging section provided in the leading end section 814 may correspond to the first imaging section 11a or the second imaging section 11b described with reference to FIG. 3, for example. In other words, in the case of configuring the endoscopic device 800 as a medical stereoscopic observation device according to the present embodiment, for example, it is sufficient to provide the imaging section provided in the leading end section 814 for each viewpoint (for example, for each viewpoint of the left eye and the right eye, respectively). Additionally, as illustrated in FIGS. 3 and 4, it is sufficient to provide each imaging section with a switching section (for example, the synchronization signal switching section 13 or the control signal switching section 33) that switches various control signals to be supplied to the imaging section provided for each viewpoint. According to such a configuration, even if there is a break in a transmission channel that supplies a control signal to one imaging section among the multiple imaging sections (for example, a transmission channel inside the universal cord 813, or a transmission channel inside the flexible tube section 816) because of damage or the like, it is still possible to supply the affected imaging section with a control signal supplied to another imaging section as a substitute.

The above thus references FIG. 14 to describe, as a second applied example of the present embodiment, an example of a case of applying a medical stereoscopic observation device according to the present embodiment to what is called a flexible endoscopic device.

Note that each of the first and second applied examples discussed above is merely one applied example of a medical stereoscopic observation device according to the present embodiment, and obviously do not limit the application of such a medical stereoscopic observation device.

7. Hardware Configuration

Figure 15:
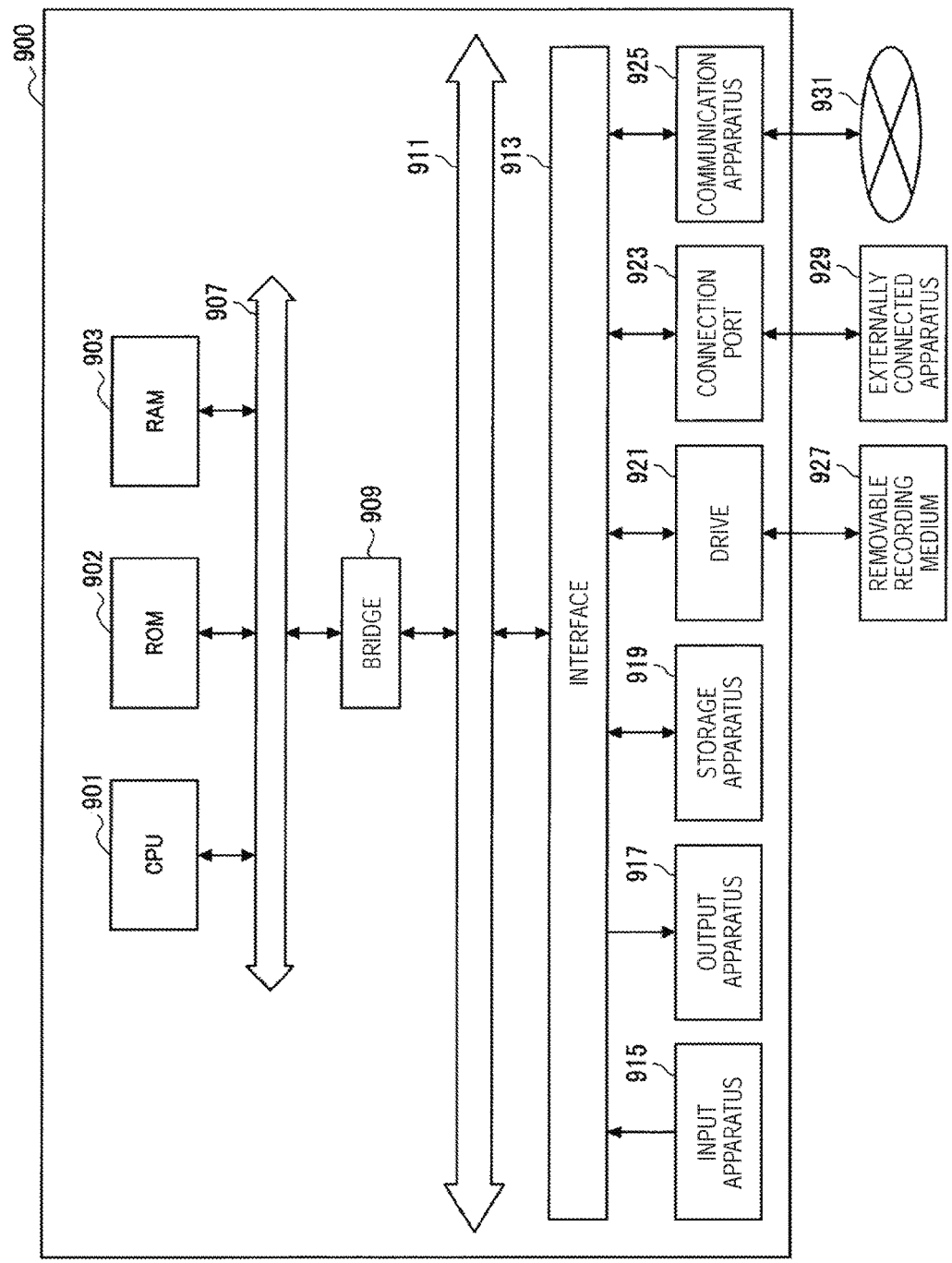
FIG. 15 is a function block diagram illustrating an example configuration of the hardware configuration of an information processing device constituting a medical stereoscopic observation system according to an embodiment.

Next, a hardware configuration of an information processing apparatus 900 constituting a medical stereoscopic observation device according to the present embodiment, such as the surgical video microscope device or the image processing device discussed earlier, will be described in detail with reference to FIG. 15. FIG. 15 is a function block diagram illustrating an example configuration of the hardware configuration of an information processing apparatus 900 constituting a medical stereoscopic observation system according to an embodiment of the present disclosure.

The information processing apparatus 900 constituting a medical stereoscopic observation system according to the present embodiment is equipped primarily with a CPU 901, ROM 903, and RAM 905. Additionally, the information processing apparatus 900 may also be equipped with a host bus 907, a bridge 909, an external bus 911, an interface 913, an input apparatus 915, an output apparatus 917, a storage apparatus 919, a drive 921, a connection port 923, and a communication apparatus 925.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 primarily stores programs that the CPU 901 uses and parameters and the like varying as appropriate during the execution of the programs. These are connected with each other via the host bus 907 configured from an internal bus such as a CPU bus or the like. Note that the first signal processing section 21a, the second signal processing section 21b, the synchronization signal generation section 23, and the combination processing section 25 discussed earlier with reference to FIG. 3 may be realized by the CPU 901, for example.

The host bus 907 is connected to the external bus 911 such as a PCI (Peripheral Component Interconnect/Interface) bus via the bridge 909. Additionally, the input apparatus 915, the output apparatus 917, the storage apparatus 919, the drive 921, the connection port 923, and the communication apparatus 925 are connected to the external bus 911 via the interface 913.

The input apparatus 915 is an operation mechanism operated by a user, such as a mouse, a keyboard, a touch panel, buttons, a switch, a lever, or a pedal. Also, the input apparatus 915 may be a remote control mechanism (a so-called remote control) using, for example, infrared light or other radio waves, or may be an externally connected apparatus 929 such as a mobile phone or a PDA conforming to the operation of the information processing apparatus 900. Furthermore, the input apparatus 915 generates an input signal based on, for example, information which is input by a user with the above operation mechanism, and is configured from an input control circuit for outputting the input signal to the CPU 901. The user of the information processing apparatus 900 can input various data to the information processing apparatus 900 and can instruct the information processing apparatus 900 to perform processing by operating this input apparatus 915.

The output apparatus 917 is configured from a device capable of visually or audibly notifying acquired information to a user. Examples of such device include display apparatuses such as a CRT display apparatus, a liquid crystal display apparatus, a plasma display apparatus, an EL display apparatus and lamps, audio output apparatuses such as a speaker and a headphone, a printer, and the like. For example, the output apparatus 917 outputs a result obtained by various processings performed by the information processing apparatus 900. More specifically, the display apparatus displays, in the form of texts or images, a result obtained by various processes performed by the information processing apparatus 900. On the other hand, the audio output apparatus converts an audio signal such as reproduced audio data and sound data into an analog signal, and outputs the analog signal.

The storage apparatus 919 is a device for storing data configured as an example of a storage unit of the information processing apparatus 900 and is used to store data. The storage apparatus 919 is configured from, for example, a magnetic storage apparatus such as a HDD (Hard Disk Drive), a semiconductor storage apparatus, an optical storage apparatus, or a magneto-optical storage apparatus. This storage apparatus 919 stores programs to be executed by the CPU 901, and various data.

The drive 921 is a reader/writer for recording medium, and is embedded in the information processing apparatus 900 or attached externally thereto. The drive 921 reads information recorded in the attached removable recording medium 927 such as a magnetic disk, an optical disk, a magneto-optical disk, or a semiconductor memory, and outputs the read information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (a registered trademark) medium. The removable recording medium 927 may be a CompactFlash (CF; a registered trademark), a flash memory, an SD memory card (Secure Digital Memory Card), or the like. Alternatively, the removable recording medium 927 may be, for example, an IC card (Integrated Circuit Card) equipped with a non-contact IC chip or an electronic appliance.

The connection port 923 is a port for allowing apparatuses to directly connect to the information processing apparatus 900. Examples of the connection port 923 include a USB (Universal Serial Bus) port, an IEEE1394 port, a SCSI (Small Computer System Interface) port, and the like. Other examples of the connection port 923 include an RS-232C port, an optical audio terminal, an HDMI (a registered trademark) (High-Definition Multimedia Interface) port, and the like. By the externally connected apparatus 929 connecting to this connection port 923, the information processing apparatus 900 directly obtains various data from the externally connected apparatus 929 and provides various data to the externally connected apparatus 929.

The communication apparatus 925 is a communication interface configured from, for example, a communication apparatus for connecting to a communication network 931. The communication apparatus 925 is, for example, a wired or wireless LAN (Local Area Network), Bluetooth (registered trademark), a communication card for WUSB (Wireless USB), or the like. Alternatively, the communication apparatus 925 may be a router for optical communication, a router for ADSL (Asymmetric Digital Subscriber Line), a modem for various communications, or the like. This communication apparatus 925 can transmit and receive signals and the like in accordance with a predetermined protocol such as TCP/IP on the Internet and with other communication apparatuses, for example. The communication network 931 connected to the communication apparatus 925 is configured from a network and the like, which is connected via wire or wirelessly, and may be, for example, the Internet, a home LAN, infrared communication, radio wave communication, satellite communication, or the like.

Heretofore, an example of the hardware configuration capable of realizing the functions of the information processing apparatus 900 constituting a medical stereoscopic observation system according to the embodiment of the present disclosure has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment. Note that, although not illustrated in FIG. 15, the various structural elements corresponding to the information processing apparatus 900 constituting a medical stereoscopic observation system (in other words, a surgical video microscope device or an image processing device) obviously are provided.

Note that it is also possible to develop a computer program for realizing the respective functions of the information processing apparatus 900 constituting a medical stereoscopic observation system according to the present embodiment as discussed above, and implement the computer program in a personal computer or the like. In addition, a computer-readable recording medium storing such a computer program may also be provided. The recording medium may be a magnetic disc, an optical disc, a magneto-optical disc, or flash memory, for example. Furthermore, the above computer program may also be delivered via a network, for example, without using a recording medium. In addition, the number of computers made to execute the computer program is not particularly limited. For example, the computer program may be executed by multiple computers (such as multiple servers, for example) in conjunction with each other.

8. Conclusion

Thus, as described above, the medical stereoscopic observation device acquires a first signal associated with a first imaging section and a second signal associated with a second imaging section via mutually different transmission channels. Additionally, the medical stereoscopic observation device switches a signal to use for a certain control between the first signal and the second signal, in accordance with the state of the transmission channel for transmitting the first signal, for example. According to such a configuration, it is possible to continue observation of an image captured by an imaging section, even under circumstances such as when there is a break in one of the transmission channels connected to each of the multiple imaging sections.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical stereoscopic observation device, including:
an acquisition section that acquires a first signal associated with a first imaging section and a second signal associated with a second imaging section via mutually different transmission channels; and
a switching section that switches a signal to use for a certain control between the first signal and the second signal, in accordance with a state of the transmission channel for transmitting the first signal.

(2) The medical stereoscopic observation device according to (1), wherein
the acquisition section acquires the first signal from an external device that controls operation of each of the first imaging section and the second imaging section, and acquires the second signal from the second imaging section.

(3) The medical stereoscopic observation device according to (2), wherein
the first signal is a first control signal for controlling operation of the first imaging section, and
the second signal is a second control signal for controlling operation of the second imaging section.

(4) The medical stereoscopic observation device according to (3), wherein
the first control signal is a synchronization signal for controlling a timing of operation of the first imaging section,
the second control signal is a synchronization signal for controlling a timing of operation of the second imaging section, and
the switching section switches a synchronization signal to supply to the first imaging section between the first control signal and the second control signal, in accordance with a state of the transmission channel for transmitting the first control signal.

(5) The medical stereoscopic observation device according to (1), wherein
the acquisition section acquires the first signal from the first imaging section, and acquires the second signal from the second imaging section.

(6) The medical stereoscopic observation device according to (5), wherein
the second signal includes information output from the second imaging section, and at least part of information output from the first imaging section.

(7) The medical stereoscopic observation device according to any one of (1) to (6), wherein
the switching section temporarily stops the switching, in accordance with a supply state of the first signal and the second signal.

(8) The medical stereoscopic observation device according to any one of (1) to (7), further including:
a notification section that notifies an external device of a detection result of a state of each of a first transmission channel for transmitting the first signal and a second transmission channel for transmitting the second signal.

(9) The medical stereoscopic observation device according to any one of (1) to (8), further including:
an adjustment section that adjusts a phase difference between the first signal and the second signal.

(10) The medical stereoscopic observation device according to any one of (1) to (9), wherein
the transmission channel for transmitting the first signal is bendably configured.

(11) The medical stereoscopic observation device according to any one of (1) to (10), further including:
a support section that supports the first imaging section and the second imaging section, wherein
at least part of the transmission channel for transmitting the first signal is supported by the support section.

(12) A medical stereoscopic observation method, including:
acquiring a first signal associated with a first imaging section and a second signal associated with a second imaging section via mutually different transmission channels; and
switching, by a processor, a signal to use for a certain control between the first signal and the second signal, in accordance with a state of the transmission channel for transmitting the first signal.

(13) A program causing a computer to execute:
acquiring a first signal associated with a first imaging section and a second signal associated with a second imaging section via mutually different transmission channels; and
switching a signal to use for a certain control between the first signal and the second signal, in accordance with a state of the transmission channel for transmitting the first signal.

(14) A medical stereoscopic observation system, including:
an imaging unit that includes a first imaging section and a second imaging section;
an image processing device that performs image processing on images captured by the first imaging section and the second imaging section;
a transmission cable that connects the imaging unit to the image processing device;
an acquisition section that acquires a first signal associated with the first imaging section via a first transmission channel provided along the transmission cable, and acquires a second signal associated with the second imaging section via a second transmission channel different from the first transmission channel; and
a switching section that switches a signal to use for a certain control between the first signal and the second signal, in accordance with a state of the first transmission channel.

(15) The medical stereoscopic observation system according to (14), further including:
a support section that supports the imaging unit, wherein
at least part of the transmission cable is supported by the support section.

(16) The medical stereoscopic observation system according to (14), further including:
an endoscope section that includes an insertion section having an elongated shape to be inserted into a test subject's body, wherein
the imaging unit is held on a front end of the insertion section, and
at least part of the transmission cable is provided along the insertion section.

What is claimed is:
1. A medical stereoscopic observation device, comprising:
processing circuitry configured to
acquire a first signal controlling a first imaging device, the first imaging device including a first image sensor and a first optical system,
acquire a second signal controlling a second imaging device, the second imaging device including a second image sensor and a second optical system, and
control switching between the first signal and the second signal, in accordance with a state of a first transmission channel for transmitting the first signal, to provide the second signal to the first imaging device via a second transmission channel from the second imaging device, the second transmission channel connecting the first imaging device and the second imaging device, wherein
the processing circuitry is provided in the first imaging device,
the processing circuitry is configured to receive the first signal directly from an external device, the external device including common signal generator circuitry configured to generate the first signal and the second signal, the external device controlling operation of each of the first imaging device and the second imaging device, and
the processing circuitry is configured to receive the second signal generated by the external device via the second imaging device and the second transmission channel to provide the second signal to the first imaging device, in response to the processing circuitry switching to the second signal in accordance with the state of the first transmission channel.

2. The medical stereoscopic observation device according to claim 1, wherein
the first signal is a first synchronization signal for controlling a timing of operation of the first imaging device,
the second signal is a second synchronization signal for controlling a timing of operation of the second imaging device, and
the processing circuitry is further configured to
switch between the first synchronization signal and the second synchronization signal in accordance with a state of the transmission channel for transmitting the first synchronization signal, and
supply a switched one of the first synchronization signal and the second synchronization signal to the first imaging device.

3. The medical stereoscopic observation device according to claim 2, wherein a value of the first synchronization signal and a value of the second synchronization signal are equal.

4. The medical stereoscopic observation device according to claim 1, wherein the processing circuitry is further configured to
acquire the first signal from the first imaging device, and
acquire the second signal from the second imaging device.

5. The medical stereoscopic observation device according to claim 4, wherein
the second signal includes information output from the second imaging device, and
at least part of information output from the first imaging device.

6. The medical stereoscopic observation device according to claim 1, wherein the processing circuitry is configured to
temporarily stop the switching in accordance with a state of the first signal and the second signal.

7. The medical stereoscopic observation device according to claim 1, wherein the processing circuitry is further configured to
notify the external device of a detection result of a state of each of the first transmission channel for transmitting the first signal and the second transmission channel for transmitting the second signal.

8. The medical stereoscopic observation device according to claim 1, wherein the processing circuitry is further configured to
adjust a phase difference between the first signal and the second signal.

9. The medical stereoscopic observation device according to claim 1, wherein
the first transmission channel for transmitting the first signal is bendably configured.

10. The medical stereoscopic observation device according to claim 1, further comprising:
a support that supports the first imaging device and the second imaging device, wherein
at least part of the first transmission channel for transmitting the first signal is supported by the support.

11. The medical stereoscopic observation device according to claim 1, wherein the second signal controlling the second imaging device is split, the second signal being transmitted to the second imaging device and to the first imaging device via the second imaging device.

12. The medical stereoscopic observation device according to claim 1, wherein the first transmission channel and the second transmission channel operatively-couple the first imaging device and the second imaging device, respectively, to a common signal generator configured to generate the first signal and the second signal.

13. The medical stereoscopic observation device according to claim 1, wherein the first transmission channel connects the first imaging device and an image processing device.

14. A medical stereoscopic observation method, comprising:
  acquiring, by processing circuitry, a first signal controlling a first imaging device, the first imaging device including a first image sensor and a first optical system;
  acquiring, by the processing circuitry, a second signal controlling a second imaging device, the second imaging device including a second image sensor and a second optical system; and
  switching, by the processing circuitry, between the first signal and the second signal in accordance with a state of a first transmission channel for transmitting the first signal, to provide the second signal to the first imaging device via a second transmission channel from the second imaging device, the second transmission channel connecting the first imaging device and the second imaging device, wherein
  the processing circuitry is provided in the first imaging device,
  the method further comprises receiving, using the processing circuitry, the first signal directly from an external device, the external device including common signal generator circuitry configured to generate the first signal and the second signal, the external device controlling operation of each of the first imaging device and the second imaging device, and
  the method further comprises receiving, by the processing circuitry, the second signal generated by the external device via the second imaging device and the second transmission channel to provide the second signal to the first imaging device, in response to the processing circuitry switching to the second signal in accordance with the state of the first transmission channel.

15. A non-transitory computer-readable storage medium storing computer-readable instructions that, when executed by a computer, cause the computer to perform a method, comprising:
  acquiring, by processing circuitry, a first signal controlling a first imaging device, the first imaging device including a first image sensor and a first optical system; and
  acquiring, by the processing circuitry, a second signal controlling a second imaging device, the second imaging device including a second image sensor and a second optical system; and
  switching, by the processing circuitry, between the first signal and the second signals in accordance with a state of a first transmission channel for transmitting the first signal, to provide the second signal to the first imaging device via a second transmission channel from the second imaging device, the second transmission channel connecting the first imaging device and the second imaging device, wherein
  the processing circuitry is provided in the first imaging device,
  the method further comprises receiving, using the processing circuitry, the first signal directly from an external device, the external device including common signal generator circuitry configured to generate the first signal and the second signal, the external device controlling operation of each of the first imagine device and the second imaging device, and
  the method further comprises receiving, by the processing circuitry, the second signal generated by the external device via the second imaging device and the second transmission channel to provide the second signal to the first imaging device, in response to the processing circuitry switching to the second signal in accordance with the state of the first transmission channel.

16. A medical stereoscopic observation system, comprising:
  an image capture device that includes a first imaging device and a second imaging device, the first imaging device including a first image sensor and a first optical system, the second imaging device including a second image sensor and a second optical system;
  an image processing device, including first processing circuitry configured to generate an imaging control parameter, that performs image processing, via first signal processing and second signal processing, on images captured by the first imaging device and the second imaging device;
  a transmission cable that connects the image capture device to the image processing device; and
  second processing circuitry configured to
    acquire a first signal controlling the first imaging device via a first transmission channel provided along the transmission cable,
    acquire a second signal controlling the second imaging device via a second transmission channel different from the first transmission channel and provided along the transmission cable, and
    control switching between the first signal and the second signals in accordance with a state of the first transmission channel for transmitting the first signal, to provide the second signal to the first imaging device via the second transmission channel from the second imaging device, the second transmission channel connecting the first imaging device and the second imaging device, wherein
  the first signal and the second signal provide the imaging control parameter,
  the second processing circuitry is provided in the first imaging device,
  the second processing circuitry is configured to receive the first signal directly from an external device the external device including common signal generator circuitry configured to generate the first signal and the second signal, the external device controlling operation of each of the first imaging device and the second imaging device, and
  the second processing circuitry is configured to receive the second signal generated by the external device via the second imaging device and the second transmission channel to provide the second signal to the first imaging device, in response to the second processing circuitry switching to the second signal in accordance with the state of the first transmission channel.

17. The medical stereoscopic observation system according to claim 16, further comprising:
  a support that supports the image capture device, wherein at least part of the transmission cable is supported by the support.

18. The medical stereoscopic observation device according to claim 16, further comprising:
an endoscope device that includes an insertion portion having an elongated shape to be inserted into a test subject's body, wherein
the image capture device is held on a front end of the insertion portion, and
at least part of the transmission cable is provided along the insertion portion.

19. The medical stereoscopic observation system according to claim 16, wherein the first signal and the second signal are generated by a common signal generator, the common signal generator being operatively-coupled to the first transmission channel and to the second transmission channel provided along the transmission cable.

* * * * *